United States Patent
Urech et al.

(10) Patent No.: US 12,098,203 B2
(45) Date of Patent: *Sep. 24, 2024

(54) HETERO-DIMERIC MULTI-SPECIFIC ANTIBODY FORMAT TARGETING AT LEAST CD3 AND HSA

(71) Applicant: Numab Therapeutics AG, Wädenswil (CH)

(72) Inventors: David Urech, Jona (CH); Tea Gunde, Zurich (CH); Sebastian Meyer, Eggenwil (CH); Christian Hess, Zurich (CH); Alexandre Simonin, Rosenau (FR)

(73) Assignee: Numab Therapeutics AG, Horgen (CH)

( * ) Notice: Subject to any disclaimer, the term of this patent is extended or adjusted under 35 U.S.C. 154(b) by 328 days.

This patent is subject to a terminal disclaimer.

(21) Appl. No.: 16/608,555

(22) PCT Filed: Jun. 4, 2018

(86) PCT No.: PCT/EP2018/064633
§ 371 (c)(1),
(2) Date: Oct. 25, 2019

(87) PCT Pub. No.: WO2018/224443
PCT Pub. Date: Dec. 13, 2018

(65) Prior Publication Data
US 2020/0181263 A1    Jun. 11, 2020

Related U.S. Application Data

(60) Provisional application No. 62/515,293, filed on Jun. 5, 2017.

(51) Int. Cl.
*C07K 16/44*    (2006.01)
*C07K 16/28*    (2006.01)
*C07K 16/32*    (2006.01)

(52) U.S. Cl.
CPC .......... *C07K 16/2809* (2013.01); *C07K 16/32* (2013.01); *C07K 2317/24* (2013.01); *C07K 2317/31* (2013.01); *C07K 2317/622* (2013.01); *C07K 2317/626* (2013.01); *C07K 2317/64* (2013.01); *C07K 2317/73* (2013.01); *C07K 2317/92* (2013.01); *C07K 2317/94* (2013.01)

(58) Field of Classification Search
CPC ........... C07K 2317/60; C07K 2317/31; C07K 16/2809; C07K 16/44
USPC ........................................... 424/133.1, 136.1
See application file for complete search history.

(56) References Cited

U.S. PATENT DOCUMENTS

| | | | | |
|---|---|---|---|---|
| 11,236,150 | B2* | 2/2022 | Meyer | C07K 16/2866 |
| 11,365,260 | B2* | 6/2022 | Cui | C07K 16/30 |
| 2016/0368987 | A1* | 12/2016 | Urech | A61P 17/04 |
| 2020/0115449 | A1* | 4/2020 | Gunde | C07K 16/32 |
| 2020/0325214 | A1* | 10/2020 | Gunde | C07K 16/244 |
| 2022/0403028 | A1* | 12/2022 | Gunde | C07K 16/32 |

FOREIGN PATENT DOCUMENTS

| | | |
|---|---|---|
| WO | 2014/206561 A1 | 12/2014 |
| WO | 2015/172800 A1 | 11/2015 |
| WO | 2016/184570 A1 | 11/2016 |
| WO | 2016/202457 A1 | 12/2016 |

OTHER PUBLICATIONS

ClinicalTrials.gov Identifier: NCT06299163, pp. 1-8; Apr. 9, 2024.*
Egan et al., "Novel multispecific heterodimeric antibody format allowing modular assembly of variable domain fragments," MABS 9(1):68-84 (Oct. 27, 2016).
Egan, "Supplementary material: Novel multispecific heterodimeric antibody format allowing modular assembly of variable domain fragments," MABS 9(1):1-3 (Oct. 27, 2016).
International Search Report and Provisional Opinion, International Application No. PCT/EP2018/064633 (12 pages).
Written Opinion of the ISA, International Application No. PCT/EP2018/064633 (9 pages).

* cited by examiner

*Primary Examiner* — Lynn A Bristol
(74) *Attorney, Agent, or Firm* — Prismatic Law Group, PLLC; Ronald J. Kamis

(57) ABSTRACT

This invention relates to a hetero-dimeric multi-specific format of multiple antibody variable domains comprising a core of two split variable domain pairs wherein both variable light domains and the two cognate variable heavy domains are positioned in tandem on two separate protein chains, respectively, and wherein one of said variable domain pairs is specific for human serum albumin and the other said variable domain pair is specific for human CD3.

25 Claims, 16 Drawing Sheets
Specification includes a Sequence Listing.

| Lane | Layout | Lane | Layout |
|---|---|---|---|
| 1 | Marker | 8 | Final sample PRO739 |
| 2 | Final sample PRO733 | 9 | |
| 3 | Final sample PRO734 | 10 | Final sample PRO741 |
| 4 | | 11 | |
| 5 | Final sample PRO736 | 12 | |
| 6 | Final sample PRO737 | 13 | Final sample PRO746 |
| 7 | Final sample PRO738 | 14 | Final sample PRO747 |

Figure 11 (contd.):
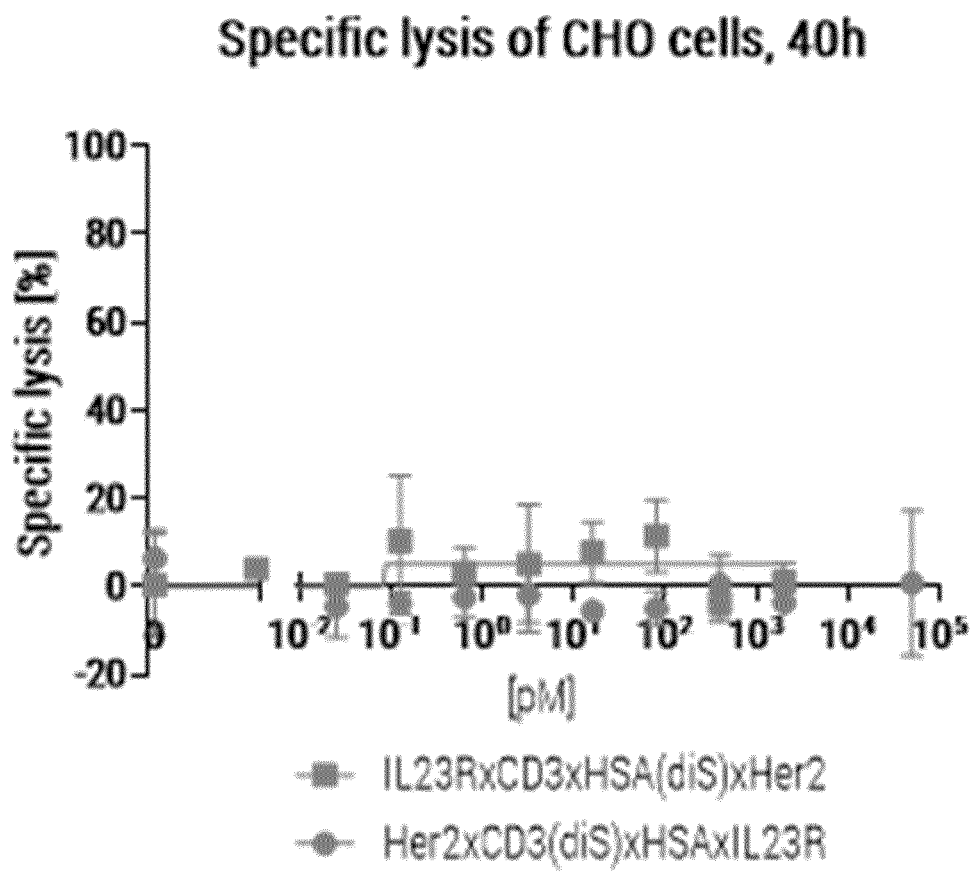

SEQUENCE LISTING

```
<160> NUMBER OF SEQ ID NOS: 30

<210> SEQ ID NO 1
<211> LENGTH: 264
<212> TYPE: PRT
<213> ORGANISM: Artificial Sequence
<220> FEATURE:
<223> OTHER INFORMATION: recombinant antibody sequence

<400> SEQUENCE: 1

Asp Ile Gln Met Thr Gln Ser Pro Ser Ser Leu Ser Ala Ser Val Gly
1               5                   10                  15

Asp Arg Val Thr Ile Thr Cys Gln Ala Ser Glu Asn Ile Tyr Ser Phe
            20                  25                  30

Leu Ala Trp Tyr Gln Gln Lys Pro Gly Lys Ala Pro Lys Leu Leu Ile
        35                  40                  45

Tyr Ser Ala Ser Lys Leu Ala Ala Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80
```

Glu Asp Phe Ala Thr Tyr Tyr Cys Gln Gln Thr Asn Arg Tyr Ser Asn
            85                  90                  95

Pro Asp Ile Tyr Asn Val Phe Gly Thr Gly Thr Lys Val Thr Val Leu
            100                 105                 110

Gly Gly Gly Gly Ser Gly Gly Gly Ser Gly Gly Gly Ser
            115                 120                 125

Gly Gly Gly Gly Ser Glu Val Gln Leu Val Glu Ser Gly Gly Gly Leu
            130                 135                 140

Val Gln Pro Gly Gly Ser Leu Arg Leu Ser Cys Ala Ala Ser Gly Ile
145                 150                 155                 160

Asp Phe Asn Ser Asn Tyr Tyr Met Cys Trp Val Arg Gln Ala Pro Gly
            165                 170                 175

Lys Gly Leu Glu Trp Ile Gly Cys Ile Tyr Val Gly Ser His Val Asn
            180                 185                 190

Thr Tyr Tyr Ala Asn Trp Ala Lys Gly Arg Phe Thr Ile Ser Arg Asp
            195                 200                 205

Asn Ser Lys Asn Thr Val Tyr Leu Gln Met Asn Ser Leu Arg Ala Glu
            210                 215                 220

Asp Thr Ala Val Tyr Tyr Cys Ala Thr Ser Gly Ser Val Leu Tyr
225                 230                 235                 240

Phe Lys Phe Trp Gly Gln Gly Thr Leu Val Thr Val Ser Ser Gly Gly
            245                 250                 255

Gly Gly Ser Gly Gly Gly Gly Ser
            260

<210> SEQ ID NO 2
<211> LENGTH: 114
<212> TYPE: PRT
<213> ORGANISM: Artificial Sequence
<220> FEATURE:
<223> OTHER INFORMATION: recombinant antibody sequence

<400> SEQUENCE: 2

Asp Ile Gln Met Thr Gln Ser Pro Ser Ser Leu Ser Ala Ser Val Gly
1               5                   10                  15

Asp Arg Val Thr Ile Thr Cys Gln Ser Ser Gln Ser Val Phe Ser Asn
            20                  25                  30

Asn Tyr Leu Ala Trp Phe Gln Gln Lys Pro Gly Gln Ser Pro Lys Arg
            35                  40                  45

Leu Ile Tyr Ser Ala Ser Thr Leu Ala Ser Gly Val Pro Ser Arg Phe
50                  55                  60

Ser Gly Ser Gly Ser Gly Thr Asp Phe Thr Leu Thr Ile Ser Ser Leu
65                  70                  75                  80

Gln Pro Glu Asp Phe Ala Thr Tyr Tyr Cys Leu Gly Ser Tyr Ala Cys
            85                  90                  95

Ser Ser Ala Asp Cys Tyr Val Phe Gly Cys Gly Thr Lys Val Thr Val
            100                 105                 110

Leu Gly

<210> SEQ ID NO 3
<211> LENGTH: 119
<212> TYPE: PRT
<213> ORGANISM: Artificial Sequence
<220> FEATURE:
<223> OTHER INFORMATION: recombinant antibody sequence

<400> SEQUENCE: 3

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Leu Ser Ser Tyr
            20                  25                  30

Asp Met Ser Trp Val Arg Gln Ala Pro Gly Lys Cys Leu Ala Trp Ile
        35                  40                  45

Gly Ala Ser Tyr Ala Ser Gly Pro Thr Tyr Tyr Ala Ser Trp Ala Lys
    50                  55                  60

Gly Arg Phe Thr Ile Ser Arg Asp Asn Ser Lys Asn Thr Val Tyr Leu
65                  70                  75                  80

Gln Met Asn Ser Leu Arg Ala Glu Asp Thr Ala Thr Tyr Phe Cys Ala
                85                  90                  95

Arg Gly Gly Trp Thr Gly Thr Ser His Ser Asn Ile Trp Gly Gln Gly
            100                 105                 110

Thr Leu Val Thr Val Ser Ser
        115

<210> SEQ ID NO 4
<211> LENGTH: 114
<212> TYPE: PRT
<213> ORGANISM: Artificial Sequence
<220> FEATURE:
<223> OTHER INFORMATION: recombinant antibody sequence

<400> SEQUENCE: 4

Asp Ile Gln Met Thr Gln Ser Pro Ser Ser Leu Ser Ala Ser Val Gly
1               5                   10                  15

Asp Arg Val Thr Ile Thr Cys Gln Ser Ser Gln Ser Val Phe Ser Asn
            20                  25                  30

Asn Tyr Leu Ala Trp Phe Gln Gln Lys Pro Gly Gln Ser Pro Lys Arg
        35                  40                  45

Leu Ile Tyr Ser Ala Ser Thr Leu Ala Ser Gly Val Pro Ser Arg Phe
    50                  55                  60

Ser Gly Ser Gly Ser Gly Thr Asp Phe Thr Leu Thr Ile Ser Ser Leu
65                  70                  75                  80

Gln Pro Glu Asp Phe Ala Thr Tyr Tyr Cys Leu Gly Ser Tyr Ala Cys
                85                  90                  95

Ser Ser Ala Asp Cys Tyr Val Phe Gly Thr Gly Thr Lys Val Thr Val
            100                 105                 110

Leu Gly

<210> SEQ ID NO 5
<211> LENGTH: 119
<212> TYPE: PRT
<213> ORGANISM: Artificial Sequence
<220> FEATURE:
<223> OTHER INFORMATION: recombinant antibody sequence

<400> SEQUENCE: 5

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Leu Ser Ser Tyr
            20                  25                  30

Asp Met Ser Trp Val Arg Gln Ala Pro Gly Lys Gly Leu Ala Trp Ile
        35                  40                  45

Gly Ala Ser Tyr Ala Ser Gly Pro Thr Tyr Tyr Ala Ser Trp Ala Lys
    50                  55                  60

Gly Arg Phe Thr Ile Ser Arg Asp Asn Ser Lys Asn Thr Val Tyr Leu
65                  70                  75                  80

Gln Met Asn Ser Leu Arg Ala Glu Asp Thr Ala Thr Tyr Phe Cys Ala
                85                  90                  95

Arg Gly Gly Trp Thr Gly Thr Ser His Ser Asn Ile Trp Gly Gln Gly
            100                 105                 110

Thr Leu Val Thr Val Ser Ser
        115

<210> SEQ ID NO 6
<211> LENGTH: 114
<212> TYPE: PRT
<213> ORGANISM: Artificial Sequence
<220> FEATURE:
<223> OTHER INFORMATION: recombinant antibody sequence

<400> SEQUENCE: 6

Asp Ile Gln Met Thr Gln Ser Pro Ser Ser Leu Ser Ala Ser Val Gly
1               5                   10                  15

Asp Arg Val Thr Ile Thr Cys Gln Ser Glu Ser Val Tyr Asn Asn
                20                  25                  30

Lys Arg Leu Ser Trp Tyr Gln Gln Lys Pro Gly Lys Ala Pro Lys Leu
            35                  40                  45

Leu Ile Tyr Thr Ala Ser Ser Leu Ala Ser Gly Val Pro Ser Arg Phe
50                  55                  60

Ser Gly Ser Gly Ser Gly Thr Asp Phe Thr Leu Thr Ile Ser Ser Leu
65                  70                  75                  80

Gln Pro Glu Asp Phe Ala Thr Tyr Tyr Cys Gln Gly Glu Phe Thr Cys
                85                  90                  95

Ser Asn Ala Asp Cys Phe Thr Phe Gly Cys Gly Thr Lys Val Thr Val
            100                 105                 110

Leu Gly

<210> SEQ ID NO 7
<211> LENGTH: 123
<212> TYPE: PRT
<213> ORGANISM: Artificial Sequence
<220> FEATURE:
<223> OTHER INFORMATION: recombinant antibody sequence

<400> SEQUENCE: 7

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Pro Leu Ser Ser Tyr
                20                  25                  30

Ala Met Ile Trp Val Arg Gln Ala Pro Gly Lys Cys Leu Glu Trp Ile
            35                  40                  45

Gly Met Ile Leu Arg Ala Gly Asn Ile Tyr Tyr Ala Ser Trp Val Lys
50                  55                  60

Gly Arg Phe Thr Ile Ser Arg Asp Asn Ser Lys Asn Thr Val Tyr Leu
65                  70                  75                  80

Gln Met Asn Ser Leu Arg Ala Glu Asp Thr Ala Val Tyr Tyr Cys Ala
                85                  90                  95

Arg Arg His Tyr Asn Arg Glu Gly Tyr Pro Ile Gly Ile Gly Asp Leu
            100                 105                 110

Trp Gly Gln Gly Thr Leu Val Thr Val Ser Ser
115                 120

<210> SEQ ID NO 8
<211> LENGTH: 114
<212> TYPE: PRT
<213> ORGANISM: Artificial Sequence
<220> FEATURE:
<223> OTHER INFORMATION: recombinant antibody sequence

<400> SEQUENCE: 8

Asp Ile Gln Met Thr Gln Ser Pro Ser Ser Leu Ser Ala Ser Val Gly
 1               5                  10                  15

Asp Arg Val Thr Ile Thr Cys Gln Ser Glu Ser Val Tyr Asn Asn
                20                  25                  30

Lys Arg Leu Ser Trp Tyr Gln Gln Lys Pro Gly Lys Ala Pro Lys Leu
            35                  40                  45

Leu Ile Tyr Thr Ala Ser Ser Leu Ala Ser Gly Val Pro Ser Arg Phe
        50                  55                  60

Ser Gly Ser Gly Ser Gly Thr Asp Phe Thr Leu Thr Ile Ser Ser Leu
65                  70                  75                  80

Gln Pro Glu Asp Phe Ala Thr Tyr Tyr Cys Gln Gly Glu Phe Thr Cys
                85                  90                  95

Ser Asn Ala Asp Cys Phe Thr Phe Gly Thr Gly Thr Lys Val Thr Val
            100                 105                 110

Leu Gly

<210> SEQ ID NO 9
<211> LENGTH: 123
<212> TYPE: PRT
<213> ORGANISM: Artificial Sequence
<220> FEATURE:
<223> OTHER INFORMATION: recombinant antibody sequence

<400> SEQUENCE: 9

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Pro Leu Ser Ser Tyr
                20                  25                  30

Ala Met Ile Trp Val Arg Gln Ala Pro Gly Lys Gly Leu Glu Trp Ile
            35                  40                  45

Gly Met Ile Leu Arg Ala Gly Asn Ile Tyr Tyr Ala Ser Trp Val Lys
        50                  55                  60

Gly Arg Phe Thr Ile Ser Arg Asp Asn Ser Lys Asn Thr Val Tyr Leu
65                  70                  75                  80

Gln Met Asn Ser Leu Arg Ala Glu Asp Thr Ala Val Tyr Tyr Cys Ala
                85                  90                  95

Arg Arg His Tyr Asn Arg Glu Gly Tyr Pro Ile Gly Ile Gly Asp Leu
            100                 105                 110

Trp Gly Gln Gly Thr Leu Val Thr Val Ser Ser
        115                 120

<210> SEQ ID NO 10
<211> LENGTH: 112
<212> TYPE: PRT
<213> ORGANISM: Artificial Sequence
<220> FEATURE:
<223> OTHER INFORMATION: recombinant antibody sequence

<400> SEQUENCE: 10

Asp Ile Gln Met Thr Gln Ser Pro Ser Ser Leu Ser Ala Ser Val Gly

```
            1               5                  10                 15
Asp Arg Val Thr Ile Thr Cys Gln Ser Ser Glu Ser Val Tyr Ser Asn
                        20                  25                 30

Asn Gln Leu Ser Trp Tyr Gln Gln Lys Pro Gly Gln Pro Pro Lys Leu
            35                  40                 45

Leu Ile Tyr Asp Ala Ser Asp Leu Ala Ser Gly Val Pro Ser Arg Phe
            50                  55                 60

Ser Gly Ser Gly Ser Gly Thr Asp Phe Thr Leu Thr Ile Ser Ser Leu
65                      70                  75                 80

Gln Pro Glu Asp Phe Ala Thr Tyr Tyr Cys Ala Gly Gly Phe Ser Ser
                        85                  90                 95

Ser Ser Asp Thr Ala Phe Gly Gly Gly Thr Lys Leu Thr Val Leu Gly
                100                 105                110
```

```
<210> SEQ ID NO 11
<211> LENGTH: 121
<212> TYPE: PRT
<213> ORGANISM: Artificial Sequence
<220> FEATURE:
<223> OTHER INFORMATION: recombinant antibody sequence

<400> SEQUENCE: 11

Glu Val Gln Leu Val Glu Ser Gly Gly Gly Leu Val Gln Pro Gly Gly
1               5                  10                 15

Ser Leu Arg Leu Ser Cys Ala Ala Ser Gly Phe Ser Leu Ser Ser Asn
            20                  25                 30

Ala Met Gly Trp Val Arg Gln Ala Pro Gly Lys Gly Leu Glu Tyr Ile
            35                  40                 45

Gly Ile Ile Ser Val Gly Gly Phe Thr Tyr Tyr Ala Ser Trp Ala Lys
            50                  55                 60

Gly Arg Phe Thr Ile Ser Arg Asp Asn Ser Lys Asn Thr Val Tyr Leu
65                      70                  75                 80

Gln Met Asn Ser Leu Arg Ala Glu Asp Thr Ala Thr Tyr Phe Cys Ala
                        85                  90                 95

Arg Asp Arg His Gly Gly Asp Ser Ser Gly Ala Phe Tyr Leu Trp Gly
                100                 105                110

Gln Gly Thr Leu Val Thr Val Ser Ser
        115                 120
```

```
<210> SEQ ID NO 12
<211> LENGTH: 112
<212> TYPE: PRT
<213> ORGANISM: Artificial Sequence
<220> FEATURE:
<223> OTHER INFORMATION: recombinant antibody sequence

<400> SEQUENCE: 12

Asp Ile Gln Met Thr Gln Ser Pro Ser Ser Leu Ser Ala Ser Val Gly
1               5                  10                 15

Asp Arg Val Thr Ile Thr Cys Gln Ser Ser Glu Ser Val Tyr Ser Asn
            20                  25                 30

Asn Gln Leu Ser Trp Tyr Gln Gln Lys Pro Gly Gln Pro Pro Lys Leu
            35                  40                 45

Leu Ile Tyr Asp Ala Ser Asp Leu Ala Ser Gly Val Pro Ser Arg Phe
            50                  55                 60

Ser Gly Ser Gly Ser Gly Thr Asp Phe Thr Leu Thr Ile Ser Ser Leu
65                      70                  75                 80
```

Gln Pro Glu Asp Phe Ala Thr Tyr Tyr Cys Ala Gly Gly Phe Ser Ser
                85                  90                  95

Ser Ser Asp Thr Ala Phe Gly Cys Gly Thr Lys Leu Thr Val Leu Gly
            100                 105                 110

<210> SEQ ID NO 13
<211> LENGTH: 121
<212> TYPE: PRT
<213> ORGANISM: Artificial Sequence
<220> FEATURE:
<223> OTHER INFORMATION: recombinant antibody sequence

<400> SEQUENCE: 13

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Leu Ser Ser Asn
            20                  25                  30

Ala Met Gly Trp Val Arg Gln Ala Pro Gly Lys Cys Leu Glu Tyr Ile
        35                  40                  45

Gly Ile Ile Ser Val Gly Gly Phe Thr Tyr Tyr Ala Ser Trp Ala Lys
    50                  55                  60

Gly Arg Phe Thr Ile Ser Arg Asp Asn Ser Lys Asn Thr Val Tyr Leu
65                  70                  75                  80

Gln Met Asn Ser Leu Arg Ala Glu Asp Thr Ala Thr Tyr Phe Cys Ala
                85                  90                  95

Arg Asp Arg His Gly Gly Asp Ser Ser Gly Ala Phe Tyr Leu Trp Gly
            100                 105                 110

Gln Gly Thr Leu Val Thr Val Ser Ser
        115                 120

<210> SEQ ID NO 14
<211> LENGTH: 110
<212> TYPE: PRT
<213> ORGANISM: Artificial Sequence
<220> FEATURE:
<223> OTHER INFORMATION: recombinant antibody sequence

<400> SEQUENCE: 14

Asp Val Val Met Thr Gln Ser Pro Ser Ser Leu Ser Ala Ser Val Gly
1               5                   10                  15

Asp Arg Val Thr Ile Thr Cys Gln Ala Ser Gln Ile Ile Ser Ser Arg
            20                  25                  30

Ser Ala Trp Tyr Gln Gln Lys Pro Gly Gln Pro Pro Lys Leu Leu Ile
        35                  40                  45

Tyr Gln Ala Ser Lys Leu Ala Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Cys Thr Tyr Ile Asp Ser Asn
                85                  90                  95

Phe Gly Ala Phe Gly Gly Gly Thr Lys Leu Thr Val Leu Gly
            100                 105                 110

<210> SEQ ID NO 15
<211> LENGTH: 121
<212> TYPE: PRT
<213> ORGANISM: Artificial Sequence
<220> FEATURE:
<223> OTHER INFORMATION: recombinant antibody sequence

```
<400> SEQUENCE: 15

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Phe Ser Ser Ser
            20                  25                  30

Tyr Trp Ile Cys Trp Val Arg Gln Ala Pro Gly Lys Gly Leu Glu Trp
        35                  40                  45

Val Gly Cys Val Phe Thr Gly Asp Gly Thr Tyr Tyr Ala Ser Trp
    50                  55                  60

Ala Lys Gly Arg Phe Thr Ile Ser Arg Asp Asn Ser Lys Asn Thr Val
65                  70                  75                  80

Tyr Leu Gln Met Asn Ser Leu Arg Ala Glu Asp Thr Ala Thr Tyr Phe
                85                  90                  95

Cys Ala Arg Pro Val Ser Val Tyr Tyr Tyr Gly Met Asp Leu Trp Gly
            100                 105                 110

Gln Gly Thr Leu Val Thr Val Ser Ser
            115                 120

<210> SEQ ID NO 16
<211> LENGTH: 14
<212> TYPE: PRT
<213> ORGANISM: Artificial Sequence
<220> FEATURE:
<223> OTHER INFORMATION: recombinant antibody sequence

<400> SEQUENCE: 16

Glu Pro Glu Pro Glu Pro Glu Pro Glu Pro Glu Pro Glu Pro
1               5                   10

<210> SEQ ID NO 17
<211> LENGTH: 14
<212> TYPE: PRT
<213> ORGANISM: Artificial Sequence
<220> FEATURE:
<223> OTHER INFORMATION: recombinant antibody sequence

<400> SEQUENCE: 17

Lys Pro Lys Pro Lys Pro Lys Pro Lys Pro Lys Pro Lys Pro
1               5                   10

<210> SEQ ID NO 18
<211> LENGTH: 11
<212> TYPE: PRT
<213> ORGANISM: Artificial Sequence
<220> FEATURE:
<223> OTHER INFORMATION: recombinant antibody sequence

<400> SEQUENCE: 18

Ser Gly Gly Gly Gly Ser Gly Gly Gly Gly Ser
1               5                   10

<210> SEQ ID NO 19
<211> LENGTH: 15
<212> TYPE: PRT
<213> ORGANISM: Artificial Sequence
<220> FEATURE:
<223> OTHER INFORMATION: recombinant antibody sequence

<400> SEQUENCE: 19

Gly Gly Gly Gly Ser Gly Gly Gly Gly Ser Gly Gly Gly Gly Ser
1               5                   10                  15
```

```
<210> SEQ ID NO 20
<211> LENGTH: 12
<212> TYPE: PRT
<213> ORGANISM: Artificial Sequence
<220> FEATURE:
<223> OTHER INFORMATION: recombinant antibody sequence

<400> SEQUENCE: 20

Ala Glu Ala Ala Ala Lys Glu Ala Ala Ala Lys Ala
1               5                   10

<210> SEQ ID NO 21
<211> LENGTH: 258
<212> TYPE: PRT
<213> ORGANISM: Artificial Sequence
<220> FEATURE:
<223> OTHER INFORMATION: recombinant antibody sequence

<400> SEQUENCE: 21

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gly Gly Thr Lys Leu Thr Val Leu Gly Gly Gly Gly
            100                 105                 110

Ser Gly Gly Gly Gly Ser Gly Gly Gly Ser Gly Gly Gly Gly Ser
        115                 120                 125

Glu Val Gln Leu Val Glu Ser Gly Gly Gly Leu Val Gln Pro Gly Gly
130                 135                 140

Ser Leu Arg Leu Ser Cys Ala Ala Ser Gly Phe Asn Ile Lys Asp Thr
145                 150                 155                 160

Tyr Ile His Trp Val Arg Gln Ala Pro Gly Lys Gly Leu Glu Trp Val
                165                 170                 175

Ala Arg Ile Tyr Pro Thr Asn Gly Tyr Thr Arg Tyr Ala Asp Ser Val
            180                 185                 190

Lys Gly Arg Phe Thr Ile Ser Ala Asp Thr Ser Lys Asn Thr Ala Tyr
        195                 200                 205

Leu Gln Met Asn Ser Leu Arg Ala Glu Asp Thr Ala Val Tyr Tyr Cys
    210                 215                 220

Ser Arg Trp Gly Gly Asp Gly Phe Tyr Ala Met Asp Tyr Trp Gly Gln
225                 230                 235                 240

Gly Thr Leu Val Thr Val Ser Ser Gly Gly Gly Gly Ser Gly Gly Gly
                245                 250                 255

Gly Ser

<210> SEQ ID NO 22
<211> LENGTH: 504
<212> TYPE: PRT
<213> ORGANISM: Artificial Sequence
<220> FEATURE:
<223> OTHER INFORMATION: recombinant antibody sequence
```

-continued

<400> SEQUENCE: 22

```
Asp Ile Gln Met Thr Gln Ser Pro Ser Ser Leu Ser Ala Ser Val Gly
1               5                   10                  15

Asp Arg Val Thr Ile Thr Cys Gln Ala Ser Glu Asn Ile Tyr Ser Phe
            20                  25                  30

Leu Ala Trp Tyr Gln Gln Lys Pro Gly Lys Ala Pro Lys Leu Leu Ile
        35                  40                  45

Tyr Ser Ala Ser Lys Leu Ala Ala Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Thr Asn Arg Tyr Ser Asn
                85                  90                  95

Pro Asp Ile Tyr Asn Val Phe Gly Thr Gly Thr Lys Val Thr Val Leu
            100                 105                 110

Gly Gly Gly Gly Ser Gly Gly Gly Ser Gly Gly Gly Gly Ser
        115                 120                 125

Gly Gly Gly Ser Glu Val Gln Leu Val Glu Ser Gly Gly Gly Leu
130                 135                 140

Val Gln Pro Gly Gly Ser Leu Arg Leu Ser Cys Ala Ala Ser Gly Ile
145                 150                 155                 160

Asp Phe Asn Ser Asn Tyr Tyr Met Cys Trp Val Arg Gln Ala Pro Gly
                165                 170                 175

Lys Gly Leu Glu Trp Ile Gly Cys Ile Tyr Val Gly Ser His Val Asn
            180                 185                 190

Thr Tyr Tyr Ala Asn Trp Ala Lys Gly Arg Phe Thr Ile Ser Arg Asp
        195                 200                 205

Asn Ser Lys Asn Thr Val Tyr Leu Gln Met Asn Ser Leu Arg Ala Glu
    210                 215                 220

Asp Thr Ala Val Tyr Tyr Cys Ala Thr Ser Gly Ser Ser Val Leu Tyr
225                 230                 235                 240

Phe Lys Phe Trp Gly Gln Gly Thr Leu Val Thr Val Ser Ser Gly Gly
                245                 250                 255

Gly Gly Ser Gly Gly Gly Gly Ser Asp Ile Gln Met Thr Gln Ser Pro
            260                 265                 270

Ser Ser Leu Ser Ala Ser Val Gly Asp Arg Val Thr Ile Thr Cys Gln
        275                 280                 285

Ser Ser Gln Ser Val Phe Ser Asn Asn Tyr Leu Ala Trp Phe Gln Gln
    290                 295                 300

Lys Pro Gly Gln Ser Pro Lys Arg Leu Ile Tyr Ser Ala Ser Thr Leu
305                 310                 315                 320

Ala Ser Gly Val Pro Ser Arg Phe Ser Gly Ser Gly Ser Gly Thr Asp
                325                 330                 335

Phe Thr Leu Thr Ile Ser Ser Leu Gln Pro Glu Asp Phe Ala Thr Tyr
            340                 345                 350

Tyr Cys Leu Gly Ser Tyr Ala Cys Ser Ala Asp Cys Tyr Val Phe
        355                 360                 365

Gly Cys Gly Thr Lys Val Thr Val Leu Gly Glu Pro Glu Pro Glu Pro
370                 375                 380

Glu Pro Glu Pro Glu Pro Glu Pro Asp Ile Gln Met Thr Gln Ser Pro
385                 390                 395                 400

Ser Ser Leu Ser Ala Ser Val Gly Asp Arg Val Thr Ile Thr Cys Gln
```

```
                405                 410                 415
Ser Ser Glu Ser Val Tyr Ser Asn Asn Gln Leu Ser Trp Tyr Gln Gln
            420                 425                 430

Lys Pro Gly Gln Pro Pro Lys Leu Leu Ile Tyr Asp Ala Ser Asp Leu
        435                 440                 445

Ala Ser Gly Val Pro Ser Arg Phe Ser Gly Ser Gly Ser Gly Thr Asp
    450                 455                 460

Phe Thr Leu Thr Ile Ser Ser Leu Gln Pro Glu Asp Phe Ala Thr Tyr
465                 470                 475                 480

Tyr Cys Ala Gly Gly Phe Ser Ser Ser Asp Thr Ala Phe Gly Gly
                485                 490                 495

Gly Thr Lys Leu Thr Val Leu Gly
            500

<210> SEQ ID NO 23
<211> LENGTH: 518
<212> TYPE: PRT
<213> ORGANISM: Artificial Sequence
<220> FEATURE:
<223> OTHER INFORMATION: recombinant antibody sequence

<400> SEQUENCE: 23

Asp Ile Gln Met Thr Gln Ser Pro Ser Ser Leu Ser Ala Ser Val Gly
1               5                   10                  15

Asp Arg Val Thr Ile Thr Cys Gln Ala Ser Glu Asn Ile Tyr Ser Phe
            20                  25                  30

Leu Ala Trp Tyr Gln Gln Lys Pro Gly Lys Ala Pro Lys Leu Leu Ile
        35                  40                  45

Tyr Ser Ala Ser Lys Leu Ala Ala Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Thr Asn Arg Tyr Ser Asn
                85                  90                  95

Pro Asp Ile Tyr Asn Val Phe Gly Thr Gly Thr Lys Val Thr Val Leu
            100                 105                 110

Gly Gly Gly Gly Gly Ser Gly Gly Gly Ser Gly Gly Gly Gly Ser
        115                 120                 125

Gly Gly Gly Gly Ser Glu Val Gln Leu Val Glu Ser Gly Gly Gly Leu
    130                 135                 140

Val Gln Pro Gly Gly Ser Leu Arg Leu Ser Cys Ala Ala Ser Gly Ile
145                 150                 155                 160

Asp Phe Asn Ser Asn Tyr Tyr Met Cys Trp Val Arg Gln Ala Pro Gly
                165                 170                 175

Lys Gly Leu Glu Trp Ile Gly Cys Ile Tyr Val Gly Ser His Val Asn
            180                 185                 190

Thr Tyr Tyr Ala Asn Trp Ala Lys Gly Arg Phe Thr Ile Ser Arg Asp
        195                 200                 205

Asn Ser Lys Asn Thr Val Tyr Leu Gln Met Asn Ser Leu Arg Ala Glu
    210                 215                 220

Asp Thr Ala Val Tyr Tyr Cys Ala Thr Ser Gly Ser Ser Val Leu Tyr
225                 230                 235                 240

Phe Lys Phe Trp Gly Gln Gly Thr Leu Val Thr Val Ser Ser Gly Gly
                245                 250                 255

Gly Gly Ser Gly Gly Gly Gly Ser Glu Val Gln Leu Val Glu Ser Gly
```

```
                260                 265                 270
Gly Gly Leu Val Gln Pro Gly Gly Ser Leu Arg Leu Ser Cys Ala Ala
            275                 280                 285

Ser Gly Phe Ser Leu Ser Ser Asn Ala Met Gly Trp Val Arg Gln Ala
        290                 295                 300

Pro Gly Lys Gly Leu Glu Tyr Ile Gly Ile Ile Ser Val Gly Gly Phe
305                 310                 315                 320

Thr Tyr Tyr Ala Ser Trp Ala Lys Gly Arg Phe Thr Ile Ser Arg Asp
                325                 330                 335

Asn Ser Lys Asn Thr Val Tyr Leu Gln Met Asn Ser Leu Arg Ala Glu
            340                 345                 350

Asp Thr Ala Thr Tyr Phe Cys Ala Arg Asp Arg His Gly Gly Asp Ser
        355                 360                 365

Ser Gly Ala Phe Tyr Leu Trp Gly Gln Gly Thr Leu Val Thr Val Ser
    370                 375                 380

Ser Lys Pro Lys Pro Lys Pro Lys Pro Lys Pro Lys Pro Lys Pro Glu
385                 390                 395                 400

Val Gln Leu Val Glu Ser Gly Gly Leu Val Gln Pro Gly Gly Ser
                405                 410                 415

Leu Arg Leu Ser Cys Ala Ala Ser Gly Phe Ser Leu Ser Ser Tyr Asp
            420                 425                 430

Met Ser Trp Val Arg Gln Ala Pro Gly Lys Cys Leu Ala Trp Ile Gly
        435                 440                 445

Ala Ser Tyr Ala Ser Gly Pro Thr Tyr Tyr Ala Ser Trp Ala Lys Gly
    450                 455                 460

Arg Phe Thr Ile Ser Arg Asp Asn Ser Lys Asn Thr Val Tyr Leu Gln
465                 470                 475                 480

Met Asn Ser Leu Arg Ala Glu Asp Thr Ala Thr Tyr Phe Cys Ala Arg
                485                 490                 495

Gly Gly Trp Thr Gly Thr Ser His Ser Asn Ile Trp Gly Gln Gly Thr
            500                 505                 510

Leu Val Thr Val Ser Ser
        515

<210> SEQ ID NO 24
<211> LENGTH: 11
<212> TYPE: PRT
<213> ORGANISM: Artificial Sequence
<220> FEATURE:
<223> OTHER INFORMATION: recombinant antibody sequence

<400> SEQUENCE: 24

Phe Gly Thr Gly Thr Lys Val Thr Val Leu Gly
1               5                   10

<210> SEQ ID NO 25
<211> LENGTH: 11
<212> TYPE: PRT
<213> ORGANISM: Artificial Sequence
<220> FEATURE:
<223> OTHER INFORMATION: recombinant antibody sequence

<400> SEQUENCE: 25

Phe Gly Gly Gly Thr Lys Leu Thr Val Leu Gly
1               5                   10

<210> SEQ ID NO 26
<211> LENGTH: 11
```

```
<212> TYPE: PRT
<213> ORGANISM: Artificial Sequence
<220> FEATURE:
<223> OTHER INFORMATION: recombinant antibody sequence

<400> SEQUENCE: 26

Phe Gly Gly Gly Thr Gln Leu Ile Ile Leu Gly
1               5                   10

<210> SEQ ID NO 27
<211> LENGTH: 11
<212> TYPE: PRT
<213> ORGANISM: Artificial Sequence
<220> FEATURE:
<223> OTHER INFORMATION: recombinant antibody sequence

<400> SEQUENCE: 27

Phe Gly Glu Gly Thr Glu Leu Thr Val Leu Gly
1               5                   10

<210> SEQ ID NO 28
<211> LENGTH: 11
<212> TYPE: PRT
<213> ORGANISM: Artificial Sequence
<220> FEATURE:
<223> OTHER INFORMATION: recombinant antibody sequence

<400> SEQUENCE: 28

Phe Gly Ser Gly Thr Lys Val Thr Val Leu Gly
1               5                   10

<210> SEQ ID NO 29
<211> LENGTH: 11
<212> TYPE: PRT
<213> ORGANISM: Artificial Sequence
<220> FEATURE:
<223> OTHER INFORMATION: recombinant antibody sequence

<400> SEQUENCE: 29

Phe Gly Gly Gly Thr Gln Leu Thr Val Leu Gly
1               5                   10

<210> SEQ ID NO 30
<211> LENGTH: 11
<212> TYPE: PRT
<213> ORGANISM: Artificial Sequence
<220> FEATURE:
<223> OTHER INFORMATION: recombinant antibody sequence

<400> SEQUENCE: 30

Phe Gly Gly Gly Thr Gln Leu Thr Ala Leu Gly
1               5                   10
```

HETERO-DIMERIC MULTI-SPECIFIC ANTIBODY FORMAT TARGETING AT LEAST CD3 AND HSA

CROSS-REFERENCE TO RELATED APPLICATIONS

This application is a 371 national phase of International Patent Application No. PCT/EP2018/064633 filed Jun. 4, 2018, which claims priority to U.S. Provisional Patent Application No. 62/515,293 filed Jun. 5, 2017, the content of which applications is incorporated herein by reference.

INCORPORATION OF SEQUENCE LISTING

This application contains a sequence listing submitted electronically via EFS-web, which serves as both the paper copy and the computer readable form (CRF) and consists of a file entitled "WRN11NP_seqlist.txt", which was created on Oct. 25, 2019, which is 32,394 bytes in size, and which is herein incorporated by reference in its entirety.

FIELD OF THE INVENTION

This invention relates to a novel hetero-dimeric multi-specific format of multiple antibody variable domains comprising a core of two split variable domain pairs wherein both variable light domains and the two cognate variable heavy domains are positioned in tandem on two separate protein chains, respectively.

BACKGROUND OF THE INVENTION

In the past forty years since the development of the first monoclonal antibodies [R17], antibodies have become an increasingly important class of biomolecules for research, diagnostic and therapeutic purposes.

Antibodies, as therapeutic agents, are evolving towards more rationally designed functionalities thus improving and expanding their inherent properties. Examples include the optimization of effector functions by glycoengineering [R18], specific localization like the transfer over the blood brain barrier [R19], or tuned half-life by e.g. increased binding to FcRn [R20].

A complementary approach of antibody functionalization is the combination of different target specificities in one molecule to generate bi- or multispecific antibodies or antibody fragments, thus allowing alternative mechanisms of action, like the retargeting of T cells, as exemplified by bispecific antibody Blinatumomab or the trispecific antibody Catumaxomab.

Despite the large number of different multispecific antibody formats that have been developed so far [R21], the current repertoire of bi- and multispecific antibody formats still leaves the industry with considerable technical challenges and little flexibility with only few formats that allow for tri- and multi-specific binding and even less formats supporting the formation of hetero-dimeric proteins.

Different multi-specific formats have been presented in the past. Conceptually these formats can be grouped into three categories: a) single-chain multi-specific formats, in which the different target binding domains are all located on one single protein chain, expressed from a single gene, b) homo-bi- and homo-multimeric formats, in which the different target-binding domains are located on identical protein chains that are assembled by the use of a multimerization domain resulting in bi-/multi-valent and optionally also multi-specific complexes, and c) hetero-dimeric formats in which the target-binding domains are located on different protein chains, and the assembly of the two protein chains is driven by a hetero-dimerization domain.

Hetero-dimeric multi-specific formats in principle offer the advantage that binding domains with different specificities and affinities can easily be tested in various combinations by simple permutation of the two hetero-dimerizing protein chains, thereby allowing for the screening for optimal combinations of specificities and affinities directly in the final format without the need for tedious cloning.

Such screening in the final product format is required in cases where the binding properties and/or potencies of the various domains need to be carefully matched to each other to achieve optimal potency of the bi-specific protein and at the same time minimize the risk for unspecific effects. In the clinical situation this would translate to optimal efficacy at minimal risk of adverse effects. Situations, where such optimal combinations are required, may for example be the concomitant blockade of two disease-driving cytokines that are produced in the course of the disease in different concentrations. In this situation, the therapeutic bi-specific protein should allow to effectively block both cytokines at one and the same therapeutic dose.

Another example, where the characteristics of the target-binding domains of a multi-specific molecule must be coordinated, is the therapy of cancer with a cytotoxic antibody targeting two cell surface targets on the tumor cells. While the two cell surface targets of the antibody in this situation may be co-expressed exclusively on cancer cells, they may be expressed individually in a variety of healthy tissues. In order to achieve best efficacy at lowest risk for adverse side effects in tumor therapy, the cytotoxic antibody should bind to a cell preferentially, when both targets are co-expressed, but should not bind to tissues expressing only one of the two targets. To achieve this, the affinities of the two target-binding domains need to be tuned such that on one hand the affinities of the individual domains to their target are too weak to result in cell lysis, and on the other hand the cooperative avidity resulting from concomitant binding of the bi-specific molecule to both targets on a cancer cell is sufficient to induce cell lysis. Due to geometrical constraints resulting from the simultaneous binding to different macromolecules immobilized on the cell surface, the combination of domains to achieve maximal cooperative binding is not only a function of affinities, but also of epitopes and may only be identified by testing different domain combinations in the actual product format.

The native IgG type antibody can be considered a homo-dimeric format.

In order to increase the number of specificities of the homo-dimeric antibody format employing the classic IgG architecture as a scaffold, additional binding moieties, such as single-chain Fvs [R15], Fvs [R16], single domains [e.g. Nanobodies: Huang et al., Expert Rev Mol Diagn. 10 (2010):777-85] or alternative scaffolds [e.g. Fynomers: Schlatter et al., MAbs. 4 (2012) 497-508] can be appended, either to the amino- or the carboxyl-terminus of both the heavy and the light chain. One advantage of this approach is that bi- to tri-specific constructs can be generated with a conventional IgG as core domain, which allows exploiting most of the manufacturing and modification technologies that have been established for conventional IgGs. Due to the homo-dimeric nature of conventional Fc regions, however, this approach will always result in at least two identical binding domains per molecule and consequently in bivalent binding to a certain target. This may not always be wanted, particularly not (a) if only cooperative binding to two targets shall result in the desired effect, of (b) if the molecular weight shall not be further increased. Furthermore, this approach oftentimes suffered from poor domain stabilities of the appended binding moieties rendering them unsuitable for pharmaceutical development.

The concept of fusing further binding domains to increase specificities can also be applied to Fab fragments [R14] or other antigen-binding fragments of IgGs [R23]. Due to the hetero-dimeric nature of the Fab, consisting of a heavy and a light chain, the Fab fragment can be used as a hetero-dimerization domain. The Fab fragment has for example been used to engineer the so-called Tribody. In this format scFv fragments are fused to the carboxyl-terminus of both the light and the heavy chain of a Fab resulting in a truly hetero-dimeric tri-specific molecule. The light chain-heavy chain association of the Fab is mainly driven by the interaction between CL-CH1, which in addition are connected though a covalent disulfide-bond [R2]. Challenges with this format are (a) the limitation of stability to the least stable component, which will most probably be the appended scFv, and (b) the limitation to maximally three target specificities.

As an approach to solve the limitations of homo-dimeric bi-specific formats, hetero-dimeric IgGs have been introduced [R31]. Simple co-expression of two different mAbs from one cell leads with very low probability to the assembly of hetero-dimeric bi-specific IgGs in which two different heavy chains will pair with each other, and the two different light chains will pair with their corresponding heavy chain [R24]. It will, however, also lead to A) the mismatch of heavy and light chains with different specificities and to B) mixtures of different heavy chain combinations resulting in mono- and bi-specific variants. To address these difficulties several approaches have been undertaken, which create an artificial asymmetry in the molecules. The "knob-into-holes" concept [R3, R4] uses engineering of the heavy chain/heavy chain or heavy chain/light chain interface to drive the association of the co-expressed chains towards the desired configuration. In another approach the CrossMab methodology [R5] allows selective pairing of an engineered light chain/heavy chain pair. A drawback of these methodologies is that any residual fraction of mismatched molecules is very difficult to separate from the product. Therefore other techniques focus on the separation problem by engineering differential binding properties for the mono- and bispecific binders [R22] and on the other hand tolerate the loss in yield caused by the stochastic distribution of variants.

A further limitation of the IgG-based hetero-dimeric formats is that they all necessarily comprise an Fc effector domain. A format in which hetero-dimerization would be driven by target binding domains directed to any target of choice would allow increasing the number of specificities/functionalities at the same or lower molecular weight. Molecules with lower molecular weights penetrate more efficiently into target tissues (e.g. solid cancers) and thus hold the promise for improved efficacy at the same or lower dose. However, smaller formats suffer from the disadvantage of having a shorter serum half-life. An alternative approach uses non-antibody fusion proteins to confer the desired multispecificity to, for example, scFv moieties. Examples of such fusion proteins are Dock-and-Lock [R25], barnase-barstar [R26], jun-fos [R27], TNF [R28], or HSA [R29]. These concepts have in common that at least one pair of domains is added that interact in a hetero-dimeric fashion to bring the bi- or multispecific binding domains together. These hetero-dimerization domains are not directly involved in target binding, nevertheless, they increase the molecular weight of the protein—similar to the constant region one (C1) in the Tribody format. Furthermore, they might come with the risk of increased immunogenicity by incorporating non-human epitopes and sequences.

In contrast to the interaction between CL and CH1 discussed above, the association of the paratope-forming VL-VH domains is generally regarded as weak. However, there are several hetero-dimeric antibody fragment concepts that are comprised exclusively of antibody variable domains. Approaches like diabodies [R6], DARTs [R10], and Tandabs [R7, R8], amongst others, offer elegant and minimalistic approaches to create homo- and hetero-dimeric bispecific and bi- to tetra-valent assemblies. The most important limitations of these formatting strategies are (a) the addition of further specificities by fusing e.g. an scFv to the amino- or the carboxyl-terminus of either chain of diabodies or DARTs could result in the intra-chain pairing of the variable light and variable heavy domains thereby rendering hetero-dimerization of the two protein chains very challenging, and (b) due to the weak domain interface binding between the variable light and the variable heavy chain often observed in the past, these formats suffered from low monomeric stability and poor producibility, so that further engineering such as the introduction of inter-domain disulfide bonds [R12] to stabilize the VL/VH interface was regarded as being necessary.

Aiming at constructing multi-specific single-chain tandem Fv antibodies, Kipriyanov et al [R30] suggested a design comprising two protein chains, each consisting of two split Fv domains arranged in the order VL-(linker1)-VH-(linker2)-VL-(linker3)-VH. For the construction of hetero-dimeric tetra-specific proteins, the hetero-dimer would consist of two protein chains with the following architecture. Chain 1: VLA-(linker1)-VHA-(linker2)-VLB-(linker3)-VHC, and chain B: VLD-(linker1)-VHD-(linker2)-VLC-(linker3)-VHB, wherein the assembly of FvB and FvC would drive hetero-dimerization of the two chains (see FIG. 10A of WO 2016/202457). In order to prevent intra-chain assembly resulting in a tandem single-chain Fv (scFv2)-like format, and to promote hetero-dimerization of two monomeric protein chains, shortened linkers at the positions "linker3" of maximally 10 amino acids have been suggested (EP1293514 A1) The proposed organization of the two split variable domains with a linker2 of at least 15 amino acids, however, results in the possibility of the second variable domains to fold back onto N-terminal domains, leading to a single-chain diabody (scDb)-like format consisting of non-matching VH/VL pairs, which in consequence would likely not be able to bind their target. In addition, there is also the potential for the formation of a hetero-dimer in which all variable heavy and light chains on protein chain 1 would pair with the variable light and heavy chains of protein chain 2, respectively, thereby preventing the formation of the terminal scFvs (scFvA and scFvD) and resulting in the pairing of non-cognate variable domains. The tandem scFv (scFv2) or scDb-type byproducts might be the reason for the very high fraction of protein observed at the apparent molecular weight of the non-multimerized protein chains [R30].

In theory the formation of scDb-like structures in the approach described above, could be further reduced by shortening also the second linker (linker2) between the two split variable domains. This would however, limit the flexibility of the construct, which in many cases would negatively impact on the range of accessible epitopes that allow for concomitant binding of two targets. These geometrical constraints are particularly limiting when two membrane proteins shall be bound at the same time.

Additionally, and most importantly however, both monomers might form homodimeric fragments (see FIG. 10B of WO 2016/202457), so that statistically up to two thirds of dimeric products could consists of the two homodimers, while only one third would consist of the desired heterodimer.

In summary, there is a well pronounced industry need for hetero-dimeric multi-specific formats that allow for simple permutation and subsequent characterization of different binding domains in the final format. Major challenges with such formats have been (a) the relatively poor efficiency of specific hetero-dimerization resulting in suboptimal production yields, and (b) the necessity to use either non target binding proteins as hetero-dimerization domains or engineered hetero-dimer Fc effector domains that come with poor flexibility in tuning serum half-life and that limit the flexibility in adding novel functionalities without increasing the molecular weight.

Thus, it was suggested that the optimal hetero-dimeric multi-specific format would exclusively consist of target binding domains and would allow for adjusting the geometry of the molecule for example by freely changing the linker lengths between the different binding domains to accommodate the geometrical constraints defined by the interaction partners (targets). As a solution to that problem, WO 2015/058861 and Egan et al., MAbs 9 (2017) 68-84 reported the development of a novel hetero-dimeric multi-specific format of multiple antibody variable domains, which comprises a core of two split variable domain pairs wherein both variable light domains and two cognate variable heavy domains are positioned in tandem on two separate protein chains, respectively, thereby driving hetero-dimerization of the two protein chains. This format has been termed "multispecific antibody-based therapeutics by cognate heterodimerization (MATCH)". Up to two additional binding domains, particularly antibody-based binding domains, such as scFv fragments, are fused to the amino- and/or the carboxyl-terminus of either protein chain, resulting in an up to hexa-specific hetero-dimeric protein.

However, while it could successfully be shown that the underlying principle permitted the generation of such hetero-dimeric multi-specific proteins based on a core comprising a variable domain pair with binding specificity for human CD3 and a variable domain pair with binding specificity for a therapeutic target, constructs such as the MATCH constructs tested in WO 2015/058861 and in Egan et al. can be expected to require, on a case-by-case basis, the fine-tuning of the properties of the hetero-dimeric multi-specific proteins, such as by identifying suitable VL and VH domain frameworks, suitable linkers, and optionally, suitable positions for the cysteine residues for the formation of interchain disulfide bonds. Such fine-tuning is thought to be necessary since it does not appear to be possible to fully predict the heterodimerization propensity of such hetero-dimeric multi-specific proteins including a novel variable domain pair. Furthermore, it is known that the mechanism of action for such kind of multispecific molecules, comprising a CD3-binding domain and at least one domain binding to an antigen expressed on the target cells, is based on the lysis of target cells upon formation of an immunological synapse. Crosslinking and clustering of CD3 receptor on the T cell by interaction with a tumor associated antigen (TAA) on the target cell membrane will lead to T cell activation and subsequent release of cytokines and cytotoxic agents into the synapse. Without wishing to be bound by theory, it is expected that the formation of such an immunological synapse is driven, or at least fundamentally influenced by the geometry of the multispecific protein and the epitopes of the respective binding domains, so that again, it does not appear to be predictable that a novel combination of variable domain pairs forming said core will work as planned. Thus, there was still an unmet need to identify a more robust method for reliably generating such hetero-dimeric multi-specific proteins.

Furthermore, the present inventors realized, that in order to increase the specificity of target cell lysis, a T cell engaging molecule may comprise, in addition to the CD3-binding domain, at least two domains concomitantly binding to antigens expressed on the surface of the target cell. For the efficient identification of two binding domains, that together bind with optimal selectivity to the target cells, by permutation of expression plasmid combinations, each encoding one of the two protein chains of the MATCH complex, the two domains must each be located on a different protein chain of the heterodimeric MATCH complex. Therefore, there was the need for identifying a core domain, driving the heterodimerization of the two chains, that would comprise domains that are not involved in target cell binding.

The solution to this problem, i.e. the identification of a defined core of two fixed variable domain pairs which can be extended by fusing one or more additional targeting moieties to the N- and/or C-termini of one or both of the single-chain proteins, has hitherto neither been shown nor suggested in the prior art.

SUMMARY OF THE INVENTION

This invention relates to a novel hetero-dimeric multi-specific format of multiple antibody variable domains comprising a core of two split variable domain pairs wherein both variable light domains and two cognate variable heavy domains are positioned in tandem on two separate protein chains, respectively, thereby driving hetero-dimerization of the two protein chains, wherein the core is formed by a first variable domain pair with specificity for human CD3 and a second variable domain pair with specificity for human serum albumin. Up to two additional binding domains, particularly antibody-based binding domains, such as scFv fragments, are fused to the amino- and/or the carboxyl-terminus of either protein chain, resulting in an up to hexa-specific hetero-dimeric protein. In addition to forming constructs that are stable and well expressed and that can be expected to exhibit a long half-life in plasma, it could surprisingly be shown that such constructs exhibit a different pharmacodynamic profile by showing slower T cells activation kinetics and reduced cytokine release, without compromising on their maximal target cell lysis capacity, when compared to a single-chain diabody (scDb) format comprising the identical CD3-binding domain and the same domain binding to the target antigen expressed on the target cells. Such reduced cytokine release at comparable effect size holds the promise for reduced adverse effects due to cytokine release and therefore for a favorable risk-to-benefit profile.

Thus, in a first aspect the present invention relates to a hetero-dimeric protein comprising a first and a second single-chain protein, wherein said first single-chain protein comprises a first amino acid sequence consisting of (from the N- to the C-terminus):

(ia) a first VL domain,
(iia) a first polypeptide linker, and
(iiia) a second VL domain, and wherein said second single-chain protein comprises a second amino acid sequence consisting of (from the N- to the C-terminus):
(ib) a first VH domain,
(iib) a second polypeptide linker, and
(iiib) a second VH domain, and
wherein said first VL domain forms a first cognate pair of variable domains with specificity to a first target antigen with either said first or said second VH domain and said second VL domain forms a second cognate pair of variable domains with specificity to a second target antigen with the other of said VH domains, wherein one of said target antigens is human serum albumin and the other said target antigen is human CD3, and wherein at least one of said first or said second single-chain protein further comprises
(iv) at least one additional domain as third functional domain that is fused via a third polypeptide linker to said first or said second amino acid sequence.

In a second aspect, the present invention relates to one or two nucleic acid sequences encoding said first and second single-chain proteins.

In a third aspect, the present invention relates to one or two vectors comprising said one or two nucleic acid sequences.

In a fourth aspect, the present invention relates to a host cell or host cells comprising said one or two vectors.

In a fourth aspect, the present invention relates to a method for producing the first and second single-chain proteins, or the hetero-dimeric protein, of the present invention, comprising (i) providing a nucleic acid or nucleic acids according to the present invention, or a vector or vectors according to the present invention, expressing said nucleic acid or nucleic acids or said vector or vectors and collecting said first and second single-chain proteins, or said hetero-dimeric protein, from the expression system, or (ii) providing a host cell or host cells of the present invention, culturing said host cell or host cells, and collecting said first and second single-chain proteins, or said hetero-dimeric protein, from the cell culture.

In a fifth aspect, the present invention relates to a pharmaceutical composition comprising the hetero-dimeric protein of the present invention and a pharmaceutically acceptable carrier.

In a sixth aspect, the present invention relates to the hetero-dimeric protein of the present invention for use in the treatment of a disease, particularly a human disease, more particularly a human disease selected from cancer, an inflammatory and an autoimmune disease, wherein at least one of said third, fourth, fifth, or sixth functional domain is able to specifically interact with a target of therapeutic relevance in the corresponding disease. In a seventh aspect the present invention relates to a method for treating a patient suffering from a disease, particularly a human disease, more particularly a human disease selected from cancer, an inflammatory and an autoimmune disease, comprising administering to a subject an effective amount of the hetero-dimeric protein of the present invention, wherein at least one of said third, fourth, fifth, or sixth functional domain is able to specifically interact with a target of therapeutic relevance in the corresponding disease.

Particular embodiments of the present invention are set forth in the appended dependent claims.

FIGURES

FIG. 1 shows the dose response of the T-cell activation in the presence of target cells at different concentrations of MATCH and reference scDb molecules. Physiological concentrations of human serum albumin were added to the cell cultures after 5 h and 30 h of incubation.

Figure 11:
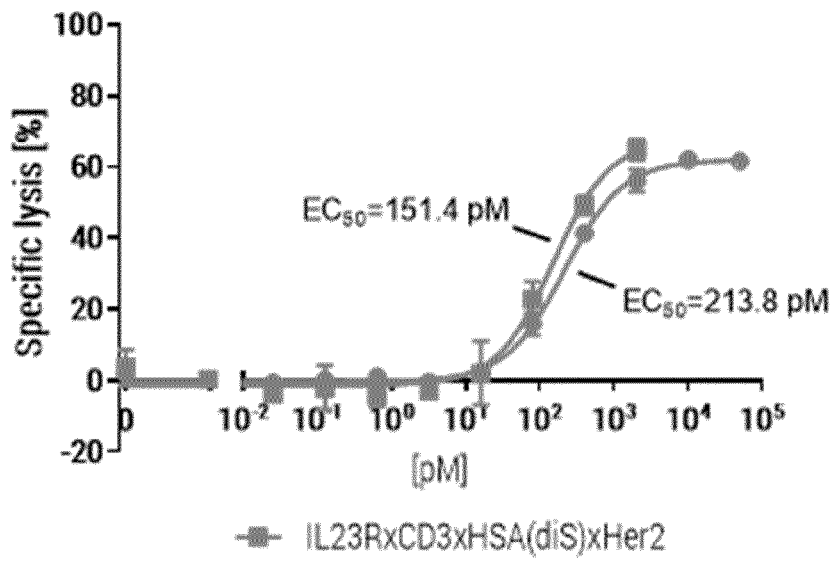
Figure 11:
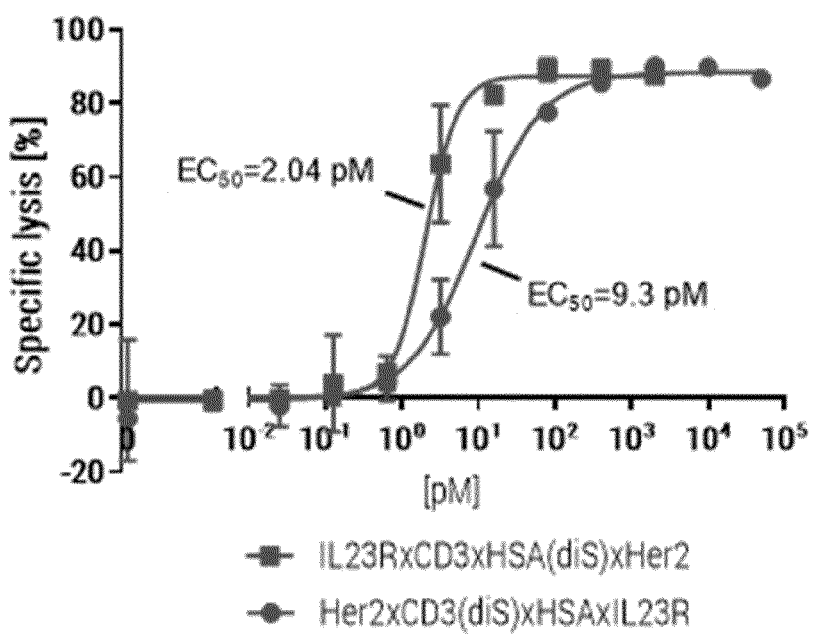

FIG. 11 shows dose-response plots of the cell lysis for two tetraspecific MATCH assemblies (PRO821 and PRO824). The upper left panel shows the specific lysis of IL23R expressing target cells, while the upper right panel shows the specific lysis of Her2 positive cells. In the lower panel the specific lysis of antigen negative cells is depicted.

Figure 12:
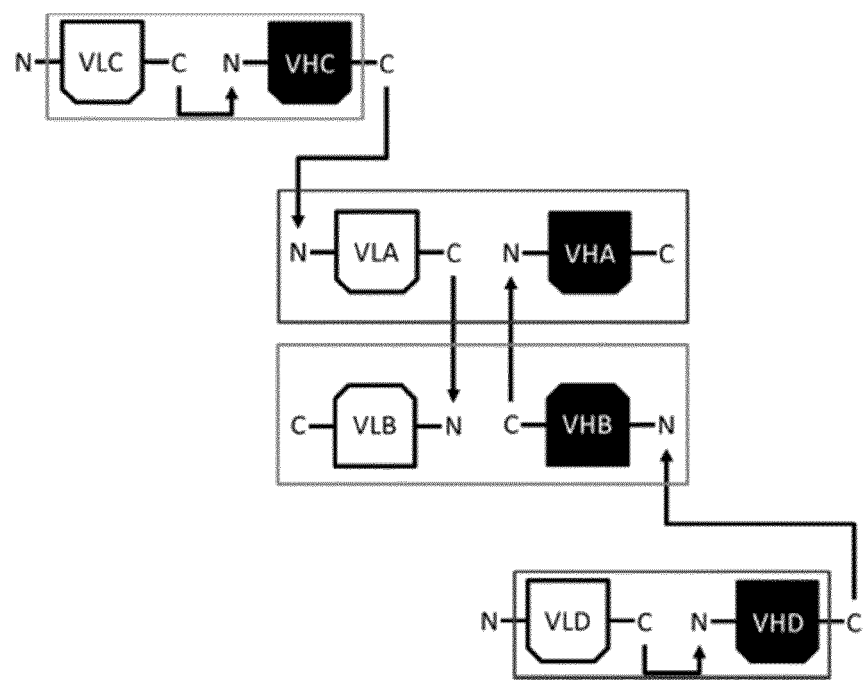
Figure 13:
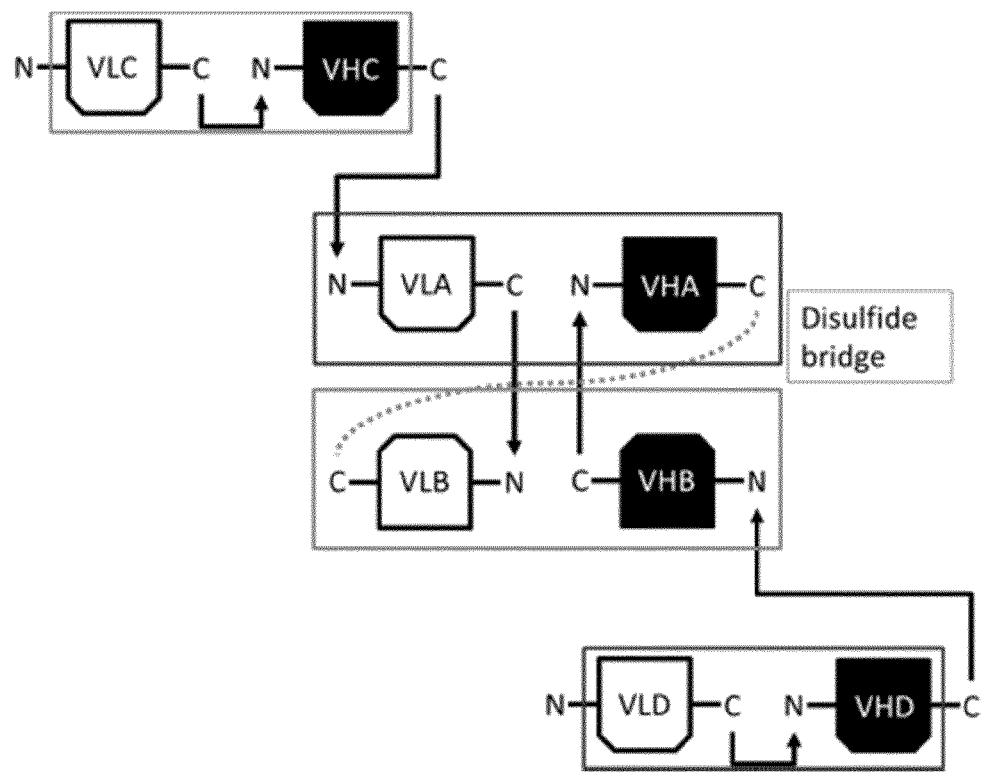
Figure 14:
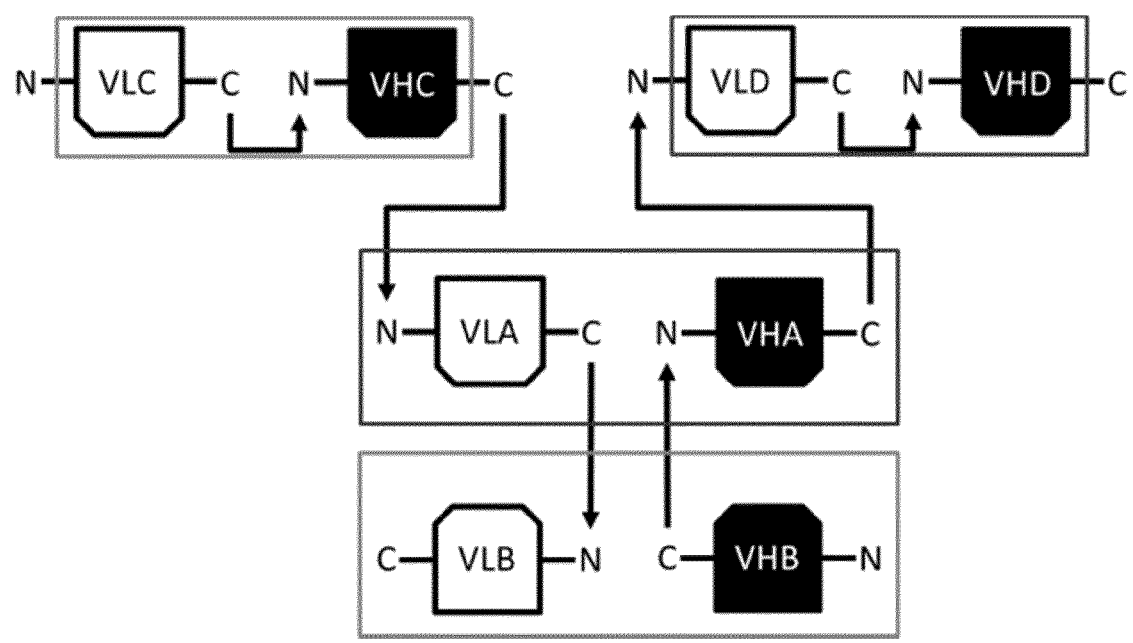
Figure 15:
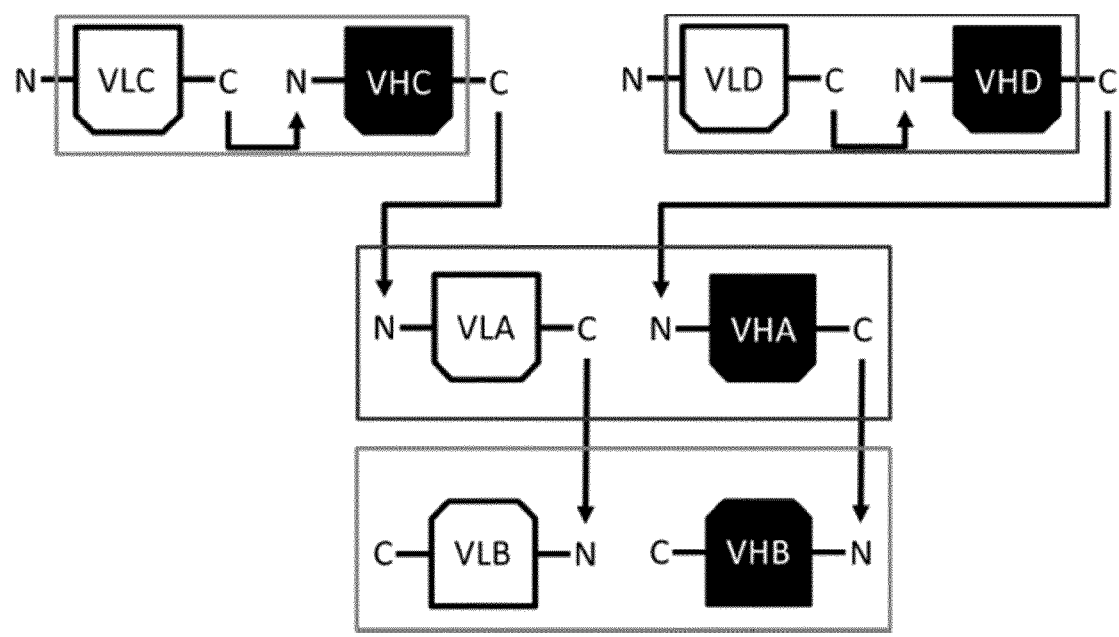

FIG. 12 shows a schematic representation of Assembly 1.
FIG. 13 shows a schematic representation of Assembly 3.
FIG. 14 shows a schematic representation of Assembly 5.
FIG. 15 shows a schematic representation of Assembly 7.

DETAILED DESCRIPTION OF THE INVENTION

Here we present a novel format exhibiting quantitative hetero-dimeric assembly of two protein chains containing multiple antibody variable domains. This format consists of a core of two split variable domain pairs (two Fv fragments), wherein both variable light domains and both variable heavy domains each are positioned on a separate protein chain, thereby driving hetero-dimerization of the two protein chains, wherein one pair of VL and VH domains is specific for human serum albumin and the other is specific for human CD3. Up to two additional binding domains, for example in the scFv format, with high intra- and inter-domain stability are fused to the amino- and/or the carboxyl-terminus of either peptide chain, resulting in an up to hexa-specific hetero-dimeric protein.

Thus, in a first aspect the present invention relates to a hetero-dimeric protein comprising a first and a second single-chain protein, wherein said first single-chain protein comprises a first amino acid sequence consisting of (from the N- to the C-terminus):
 (ia) a first VL domain,
 (iia) a first polypeptide linker, and
 (iiia) a second VL domain, and
wherein said second single-chain protein comprises a second amino acid sequence consisting of (from the N- to the C-terminus):
 (ib) a first VH domain,
 (iib) a second polypeptide linker, and
 (iiib) a second VH domain, and
wherein said first VL domain forms a first cognate pair of variable domains with specificity to a first target antigen with either said first or said second VH domain, and said second VL domain forms a second cognate pair of variable domains with specificity to a second target antigen with the other of said VH domains, wherein one of said target antigens is human serum albumin and the other said target antigen is human CD3,
and wherein at least one of said first or said second single-chain protein further comprises
 (iv) at least one additional domain as third functional domain that is fused via a third polypeptide linker to said first or said second amino acid sequence.

Throughout this specification and the claims which follow, unless the context requires otherwise, the word "comprise", and variations such as "comprises" and "comprising", will be understood to imply the inclusion of a stated integer, composition or step or group of integers or steps, while any additional integer, composition or step or group of integers, compositions or steps may optionally be present as well, including embodiments, where no additional integer, composition or step or group of integers, compositions or steps are present. With respect to such latter embodiments, the term "comprising" thus includes the narrower term "consisting of".

Several documents are cited throughout the text of this specification. Each of the documents cited herein (including all patents, patent applications, scientific publications, manufacturer's specifications, instructions, GenBank Accession Number sequence submissions etc.), whether supra or infra, is hereby incorporated by reference in its entirety to the extent possible under the respective patent law. Nothing herein is to be construed as an admission that the invention is not entitled to antedate such disclosure by virtue of prior invention.

In the context of the present invention, the terms "VL domain" and "VH domain" refer to the variable light chain domain, and the variable heavy chain domain, respectively, of antibodies. In the context of the present invention, the term "antibody" refers to immunoglobulin molecules and immunologically active portions of immunoglobulin molecules, i.e. molecules that contain an antigen binding site that specifically binds to an antigen, i.e. including antibody portions comprising at least an antigen-binding fragment of an antibody.

In the context of the present invention, an antibody, or any binding molecule in general, is considered to "specifically bind" to an antigen (in the case of an antibody), or to a cognate binding partner (in the case of a binding molecule in general), if it has a dissociation constant $K_D$ to said antigen/cognate binding partner as target of 100 μM or less, preferably 50 μM or less, preferably 30 μM or less, preferably 20 μM or less, preferably 10 μM or less, preferably 5 μM or less, more preferably 1 μM or less, more preferably 900 nM or less, more preferably 800 nM or less, more preferably 700 nM or less, more preferably 600 nM or less, more preferably 500 nM or less, more preferably 400 nM or less, more preferably 300 nM or less, more preferably 200 nM or less, even more preferably 100 nM or less, even more preferably 90 nM or less, even more preferably 80 nM or less, even more preferably 70 nM or less, even more preferably 60 nM or less, even more preferably 50 nM or less, even more preferably 40 nM or less, even more preferably 30 nM or less, even more preferably 20 nM or less, and even more preferably 10 nM or less. In the context of the present invention, the term "functional domains" refers to a proteinaceous domain having a predefined function, such as enzymatic activity or specific binding to a cognate ligand, wherein said proteinaceous domain is a structured domain having at least a secondary structure element. Methods for the determining the presence of secondary structure in polypeptides or proteins, such as X-ray crystallography, circular dichroism (CD), vibrational circular dichroism (VCD), NMR, or FT-IR, or for predicting the presence of secondary structure in polypeptides, such as PEP-FOLD (Shen et al., J. Chem. Theor. Comput. 10 (2014) 4745-4758) are well known to the practitioner in the art. In particular embodiments, said proteinaceous domain is a structured domain having a tertiary structure. In particular embodiments, said proteinaceous domain comprises at least about 20 amino acid residues (see Heitz et al., Biochemistry 38 (1999) 10615-25), particularly at least about 50 amino acid residues, more particularly at least about 100 amino acid residues. In particular embodiments, a functional domain is a proteinaceous domain that specifically binds to a cognate ligand. In particular embodiments, the functional domain is an antibody or an immunologically active portion of an antibody that specifically binds to an antigen.

In the context of the present invention, the term "polypeptide linker" refers to a linker consisting of a chain of amino acid residues linked by peptide bonds that is connecting two domains, each being attached to one end of the linker. In particular embodiments, the polypeptide linker has a continuous chain of between 2 and 30 amino acid residues (e.g. 2, 3, 4, 5, 6, 7, 8, 9, 10, 11, 12, 13, 14, 15, 16, 17, 18, 19, 20, 21, 22, 23, 24, 25, 26, 27, 28, 29, or 30 amino acid residues). In particular embodiments, the polypeptide linker is non-structured polypeptide. As mentioned above, methods for the determining the presence of secondary structure in polypeptides, such as X-ray crystallography, circular dichroism (CD), vibrational circular dichroism (VCD), NMR, or FT-IR, or for predicting the presence of secondary structure in polypeptides, such as PEP-FOLD (Shen et al., J. Chem. Theor. Comput. 10 (2014) 4745-4758) are well known to the practitioner in the art. In particular embodiments, a linker consists of amino acid residues selected from glycine and serine residues.

This invention is characterized by the following:
 The use of antibody variable domains to create a hetero-dimeric format, where at least two VL domains are located on one protein chain while the corresponding VH domains are located on a second protein chain.
 The hetero-dimeric core domain allows appending of additional functional domains, such as binding domains, to create tri-, tetra-, penta- or hexaspecific entities.
 Multiple examples for highly efficient pairing of the hetero-dimeric core assembly.
 Simple solution to combinatorial screening of multiple binding-domain pools that share a common hetero-dimeric core domain.

In a particular embodiment, the invention relates to a hetero-dimeric protein wherein said first or said second single-chain protein further comprises
   (v) a fourth functional domain that is fused via a fourth polypeptide linker to said first or said second amino acid sequence.

In a particular embodiment, the invention relates to a hetero-dimeric protein wherein said first or said second single-chain protein further comprises
   (vi) a fifth functional domain that is fused via a fifth polypeptide linker to said first or said second amino acid sequence.

In a particular embodiment, the invention relates to a hetero-dimeric protein wherein said first or said second single-chain protein further comprises
   (vii) a sixth functional domain that is fused via a sixth polypeptide linker to said first or said second amino acid sequence.

In particular embodiments, said hetero-dimeric protein comprises said third and said fourth functional domain. In such embodiments, said hetero-dimeric protein is tetravalent, in particular embodiments, said hetero-dimeric protein is tetraspecific.

In particular embodiments, said hetero-dimeric protein comprises said third, said fourth, said fifth and said sixth functional domain. In such embodiments, said hetero-dimeric protein is hexavalent, in particular embodiments, said hetero-dimeric protein is hexaspecific.

In particular embodiments, said hetero-dimeric protein does not comprise a cognate pair of a first and a second immunoglobulin constant domain, wherein said first immunoglobulin constant domain is comprised in said first single-chain protein and wherein said second immunoglobulin constant domain is comprised in said second single-chain protein. In particular embodiments, at least one of said first and said second single-chain proteins does not comprise an immunoglobulin constant domain. In a particular embodiment, both said first and said second single-chain proteins do not comprise an immunoglobulin constant domain.

In particular embodiments, said hetero-dimeric protein does not comprise a cognate pair of a first proteinaceous interaction domain comprised in said first single-chain protein and a second proteinaceous interaction domain comprised in said second single-chain protein other than the cognate pairs of (i) said first VL domain and said first VH domain and (ii) said second VL domain and said second VH domain.

In particular embodiments, said hetero-dimeric protein, wherein at least one of said third, said fourth, said fifth and said sixth functional domains is binding to a target antigen expressed on the surface of a target cell, triggers reduced cytokine levels at the time point of similar T cell activation as assessed by measuring Luciferase activity in Jurkat T cells expressing the Luciferase reporter gene under the control of NFAT in vitro in presence of physiological concentrations of HSA, when compared to a single-chain diabody (scDb) comprising the same target antigen-binding domain and the same CD3-binding domain.

In particular embodiments, said cytokines are T cell derived cytokines associated with cytokine release syndrome, such as IL-2, IL-10, IL-6, TNF-alpha and/or interferon-gamma, preferably IL-2. In particular embodiments, said cytokine levels are at least two-fold, preferably three-fold, more preferably four-fold and most preferably five-fold lower, when compared to the scDb. In particular embodiments, the determination of Luciferase activity and of cytokine levels is performed as described in the Examples.

In particular embodiments, said hetero-dimeric protein, wherein at least one of said third, said fourth, said fifth and said sixth functional domains is binding to a target antigen expressed on the surface of a target cell, demonstrates a slower kinetic to reach similar T cell activation as assessed by measuring Luciferase activity in Jurkat T cells expressing the Luciferase reporter gene under the control of NFAT in vitro in presence of physiological concentrations of HSA, when compared to a single-chain diabody (scDb) comprising the same target antigen-binding domain and the same CD3-binding domain. In particular embodiments, said kinetics are at least two-fold, preferably three-fold and most preferably four-fold slower compared to the scDb. In particular embodiments, the determination of Luciferase activity and of cytokine levels is performed as described in the Examples.

In particular embodiments, said hetero-dimeric protein, wherein at least one of said third, said fourth, said fifth and said sixth functional domains is binding to a target antigen expressed on the surface of a target cell, leads to reduced cytokine levels at the time point of similar T cell activation as assessed by CD69 expression in vitro in presence of physiological concentrations of HSA, when compared to a single-chain diabody (scDb) comprising the same target antigen-binding domain and the same CD3-binding domain. In particular embodiments, said cytokines are T cell derived cytokines associated with cytokine release syndrome, such as IL-2, IL-10, IL-6, TNF-alpha and/or interferon-gamma, preferably IL-2. In particular embodiments, said cytokine levels are at least two-fold, preferably three-fold, more preferably four-fold and most preferably five-fold lower, when compared to the scDb. In particular embodiments, the determination of CD69 expression and of cytokine levels is performed as described in the Examples.

In particular embodiments, said hetero-dimeric protein, wherein at least one of said third, said fourth, said fifth and said sixth functional domains is binding to a target antigen expressed on the surface of a target cell, leads to reduced cytokine levels at the time point of similar extent of target cell lysis in vitro in presence of physiological concentrations of HSA, when compared to a single-chain diabody (scDb) comprising the same target antigen-binding domain and the same CD3-binding domain. In particular embodiments, said cytokines are T cell derived cytokines associated with cytokine release syndrome, such as IL-2, IL-10, IL-6, TNF-alpha and/or interferon-gamma, preferably IL-2. In particular embodiments, said cytokine levels are at least two-fold, preferably three-fold, more preferably four-fold and most preferably five-fold lower, when compared to the scDb. In particular embodiments, the determination of cytokine levels is performed as described in the Examples.

In particular embodiments, said hetero-dimeric protein, wherein at least one of said third, said fourth, said fifth and said sixth functional domains is binding to a target antigen expressed on the surface of a target cell, demonstrates a slower kinetic to reach similar extent of target cell lysis in vitro in presence of physiological concentrations of HSA, when compared to a single-chain diabody (scDb) comprising the same target antigen-binding domain and the same CD3-binding domain. In particular embodiments, said kinetics are at least two-fold, preferably three-fold and most preferably four-fold slower compared to the scDb. In particular embodiments, the determination of the kinetics of target cell lysis is performed as described in the Examples.

In particular embodiments, said hetero-dimeric protein, wherein at least one of said third, said fourth, said fifth and said sixth functional domains is binding to a target antigen expressed on the surface of a target cell, has the capacity to reach similar maximal target cell lysis, when compared to a single-chain diabody (scDb) comprising the same target antigen-binding domain and the same CD3-binding domain. In particular embodiments, the determination of target cell lysis is performed as described in the Examples.

In particular embodiments, said first polypeptide linker consists of from 5 to 20 amino acid residues, particularly from of 6 to 15 amino acid residues. In particular embodiments, said polypeptide linker has the sequence $(G_mS)_n$; with m being independently selected from 2, 3, and 4; and n being selected from 1, 2, 3, 4, and 5.

In particular other embodiments, said first polypeptide linker consists of from 11 to 20 amino acid residues, particularly from of 11 to 15 amino acid residues. In particular embodiments, said polypeptide linker has the sequence $(G_mS)_n$; with m being independently selected from 2, 3, and 4; and n being selected from 3, 4, and 5.

In particular embodiments, said second polypeptide linker consists of from 5 to 20 amino acid residues, particularly from of 6 to 15 amino acid residues. In particular embodiments, said polypeptide linker has the sequence $(G_mS)_n$; with m being independently selected from 2, 3, and 4; and n being selected from 1, 2, 3, 4, and 5.

In particular other embodiments, said second polypeptide linker consists of from 11 to 20 amino acid residues, particularly from of 11 to 15 amino acid residues. In particular embodiments, said polypeptide linker has the sequence $(G_mS)_n$; with m being independently selected from 2, 3, and 4; and n being selected from 3, 4, and 5.

In particular embodiments, said third, fourth, fifth and/or sixth polypeptide linkers independently consist of from 8 to 20 amino acid residues, particularly from of 10 to 15 amino acid residues. In particular embodiments, said polypeptide linkers independently have the sequence $(G_mS)_n$; with m being independently selected from 2, 3, and 4, particularly 4; and n being selected from 1, 2, 3, 4, and 5, particularly from 2 and 3.

In particular embodiments, said first VL domain (ia) and said first VH domain (ib) form a first cognate pair of variable domains with specificity to a first target antigen, and said second VL domain (iia) and said second VH domain (iib) form a second cognate pair of variable domains with specificity to a second target antigen. In such embodiment, said first and said second single-chain protein form said heterodimeric protein in a parallel arrangement of said single-chain proteins (see FIG. 15).

In particular such embodiments, said first polypeptide linker consists of from 10 to 20 amino acid residues, particularly from of 12 to 17 amino acid residues, particularly of 15 amino acid residues. In particular embodiments, said polypeptide linker has the sequence $(G_mS)_n$; with m being independently selected from 2, 3, and 4, particularly 4; and n being selected from 1, 2, 3, 4, and 5, particularly 3.

In particular such embodiments, said second polypeptide linker consists of from 10 to 20 amino acid residues, particularly from of 12 to 17 amino acid residues, particularly of 15 amino acid residues. In particular embodiments, said polypeptide linker has the sequence $(G_mS)_n$; with m being independently selected from 2, 3, and 4, particularly 4; and n being selected from 1, 2, 3, 4, and 5, particularly 3.

In particular such embodiments, said third, fourth, fifth and/or sixth polypeptide linkers independently consist of from 10 to 20 amino acid residues, particularly from of 12 to 17 amino acid residues, particularly of 15 amino acid residues. In particular embodiments, said polypeptide linker has the sequence $(G_mS)_n$; with m being independently selected from 2, 3, and 4, particularly 4; and n being selected from 1, 2, 3, 4, and 5, particularly 3.

In particular other embodiments, said first VL domain (ia) and said second VH domain (iib) form a first cognate pair of variable domains with specificity to a first target antigen, and said second VL domain (iia) and said first VH domain (ib) form a second cognate pair of variable domains with specificity to a second target antigen. In such embodiment, said first and said second single-chain protein form said heterodimeric protein in an anti-parallel arrangement of said single-chain proteins (see FIG. 12 to 14).

In particular such embodiments, said first polypeptide linker consists of from 5 to 12 amino acid residues, particularly from of 5 to 10 amino acid residues, particularly of 6 amino acid residues. In particular embodiments, said polypeptide linker has the sequence $(G_mS)_n$; with m being independently selected from 2, 3, and 4, particularly 2; and n being selected from 1, 2, 3, 4, and 5, particularly 2.

In particular such embodiments, said second polypeptide linker consists of from 5 to 12 amino acid residues, particularly from of 6 to 10 amino acid residues, particularly of 8 amino acid residues. In particular embodiments, said polypeptide linker has the sequence $(G_mS)_n$; with m being independently selected from 2, 3, and 4, particularly 3; and n being selected from 1, 2, 3, 4, and 5, particularly 2.

In particular such embodiments, said third, fourth, fifth and/or sixth polypeptide linkers independently consist of from 10 to 20 amino acid residues, particularly from of 8 to 12 amino acid residues, particularly of 10 amino acid residues. In particular embodiments, said polypeptide linker has the sequence $(G_mS)_n$; with m being independently selected from 2, 3, and 4, particularly 4; and n being selected from 1, 2, 3, 4, and 5, particularly 2.

In another particular embodiment of the anti-parallel arrangement, said first and said second polypeptide linker each consists of from 10 to 20 amino acid residues comprising between 40 and 60% charged residues, particularly from of 12 to 16 amino acid residues comprising 50% charged residues, in each case, wherein the two linkers are able to interact by forming interchain pairs of positively and negatively charged residues. In particular embodiments, the charged residues on one of said first and second linkers are exclusively positively charged residues, and the charged residues on the other of said first and second linkers are exclusively negatively charged residues, particularly wherein said first and second linkers are selected from SEQ ID NOs. 16 and 17.

In particular embodiments, said third, fourth, fifth and/or sixth functional domains are independently selected from the list of: binding domains, toxins, enzymes, hormones, and signaling proteins.

In particular embodiments, said third, fourth, fifth and/or sixth functional domains are independently selected from binding domains.

In particular such embodiments, binding domains are independently selected from the list of: antibody-based binding domains including but not limited to scFv, Fab and single antibody variable domains, single domain antibodies based on the VNAR structure from shark, and binding domains based on alternative scaffolds including but limited to ankyrin-based domains, fynomers, avimers, anticalins, fibronectins, and binding sites being built into constant regions of antibodies (e.g. f-star technology; see, for example, Wozniak-Knopp et al., Protein Eng. Des. Sel. 23 (2010) 289-297).

In particular such embodiments, said binding domains are antibody-based binding domains selected from: single-chain Fv fragments and single antibody variable domains.

In certain such embodiments, the order of variable domain in such a single chain Fv fragment is selected from (from N-terminus to C-terminus) VL-(linker)-VH and VH-(linker)-VL. In certain embodiments, the order of variable domains is the same for all single-chain Fv fragments comprised in the hetero-dimeric protein. In certain embodiments, three VL domains are linked to each other by said first polypeptide linker and one of said third, fourth and fifth polypeptide linkers, respectively, for example where a single-chain Fv fragment in the order VL-(linker)-VH is C-terminal from said first amino acid sequence. In certain embodiments, three VH domains are linked to each other by said second polypeptide linker and one of said third, fourth and fifth polypeptide linkers, respectively, for example where a single-chain Fv fragment in the order VL-(linker)-VH is N-terminal from said second amino acid sequence (see FIGS. 12, 13 and 15). Thus, in certain embodiments at least one of said first and said second single-chain proteins comprises an amino acid sequence consisting of three VL domains or three VH domains, respectively, linked by two polypeptide linkers.

In certain other embodiments, the variable domain of any such antibody-based binding domain that is directly linked via the corresponding linker to the N- and/or the C-terminus of said first or second amino acid sequence is (a) a VH domain in case that it is fused to said first amino acid sequence, and (b) a VL domain in case that it is fused to said second amino acid sequence. Thus, a VH domain is fused to the N- and/or the C-terminus of a VL-linker-VL core region, and a VL domain is fused to the N- and/or the C-terminus of a VH-linker-VH core region (see, for example, FIG. 14).

In particular embodiments, said third, fourth, fifth and/or sixth binding domains are single-chain Fv fragments.

In particular such embodiments, the polypeptide linker connecting the variable domains of said single-chain Fv fragments consists of between 15 and 25 amino acid residues, particularly 20 amino acid residues. In particular embodiments, said polypeptide linker has the sequence (GGGGS)$_n$, with n being selected from 3, 4, and 5, particularly 4.

In particular embodiments, the at least one of said antibody variable domains comprises CDR regions derived from a parental rabbit antibody, as evidenced by specific patterns inherent to rabbit CDRs.

In particular embodiments, at least one of said antibody variable domains comprises human framework regions.

In particular embodiments, said first single-chain protein and said second single-chain protein are cross-linked by at least one disulfide bond.

In particular embodiments, said disulfide bond is formed between a first cysteine residue flanking said first or said second VL domain and a second cysteine residue flanking said first or said second VH domain.

In particular embodiments, said disulfide bond is formed between a first cysteine residue comprised in a framework region of said first or said second VL domain and a second cysteine residue comprised in a framework region of said first or said second VH domain.

In particular embodiments, said first cysteine residue is located at position 141 of said first or said second VL domain and said second cysteine residue is located at position 51 of said first or said second VH domain.

In the context of the present invention, the numbering system used for antibody variable domains is based on the numbering system ("AHo numbering") according to Honegger and Pluckthun (A. Honegger & A. Pluckthun. "Yet another numbering scheme for immunoglobulin variable domains: An automatic modeling and analysis tool". J. Mol. Biol, 309 (2001)657-670).

In particular embodiments, said cognate pair of variable domains with specificity for human serum albumin comprises the three VL CDRs present in one of the VL protein sequences selected from SEQ ID NOs: 10, 12, and 14 in a human antibody VL framework, wherein the VL framework comprises $V_K$ frameworks FR1, FR2 and FR3, particularly $V_K1$ frameworks, and a framework FR4, which is selected from a $V_K$ FR4, particularly $V_K1$ FR4, and a VA framework 4, and the three VH CDRs present in one of the VH protein sequences selected from SEQ ID NOs: 11, 13, and 15 in a human antibody VH framework, particularly a VH3 framework.

In the context of the present invention, the assignment to Vκ, Vλ and/or VH frameworks is performed by alignment with the sequences of human antibodies shown in WO 97/08320. The definition of the frameworks and CDRs is used in accordance with Honegger & Pluckthun, loc. cit.

In particular such embodiments, at least one of said VL domains comprises (i) human $V_K$ framework regions FR1 to FR3, particularly human $V_K1$ framework regions FR1 to FR3; (ii) CDR domains CDR1, CDR2 and CDR3; and (iii) a framework region IV, which is selected from
 a. a human Vλ germ line sequence for framework region IV, particularly a Vλ germ line sequence selected from the list of SEQ ID NO: 24 to 30 (SEQ ID NO. 16 to 22 according to WO 2014/206561);
 b. a VA-based sequence, which is (bi) a consensus Vλ sequence from human Vλ germ line sequences for framework region IV, particularly SEQ ID NO: 25 (SEQ ID NO. 17 according to WO 2014/206561); or (bii) a consensus Vλ sequence from rearranged human Vλ sequences for framework region IV, particularly a Vλ consensus sequence selected from the list of SEQ ID NO: 24 and 25 (SEQ ID NO. 16 and 17 according to WO 2014/206561); and
 c. a Vλ-based sequence, which has one or two mutations, particularly one mutation, compared to the closest human Vλ germ line sequence for framework region IV.

In a particular embodiment, said cognate pair of variable domains with specificity for human serum albumin comprises (i) a VL domain exhibiting at least 60, 70, 80, 90, 91, 92, 93, 94, 95, 96, 97, 98 or 99 percent, preferably at least 90 percent, sequence identity to the VL sequence according to SEQ ID NO: 10 or SEQ ID NO: 12 or SEQ ID NO: 14, and/or (ii) a VH domain exhibiting at least 60, 70, 80, 90, 91, 92, 93, 94, 95, 96, 97, 98 or 99 percent, preferably at least 90 percent, sequence identity to the VH sequence according to SEQ ID NO: 11 or SEQ ID NO: 13 or SEQ ID NO: 15.

In a particular embodiment, said cognate pair of variable domains with specificity for human serum albumin comprises (i) a VL domain exhibiting at least 60, 70, 80, 90, 91, 92, 93, 94, 95, 96, 97, 98 or 99 percent, preferably at least 90 percent, sequence identity to the VL sequence according to SEQ ID NO: 10, and a VH domain exhibiting at least 60, 70, 80, 90, 91, 92, 93, 94, 95, 96, 97, 98 or 99 percent, preferably at least 90 percent, sequence identity to VH sequence according to SEQ ID NO: 11; or (ii) a VL domain exhibiting at least 60, 70, 80, 90, 91, 92, 93, 94, 95, 96, 97, 98 or 99 percent, preferably at least 90 percent, sequence identity to the VL sequence according to SEQ ID NO: 12, and a VH domain exhibiting at least 60, 70, 80, 90, 91, 92, 93, 94, 95, 96, 97, 98 or 99 percent, preferably at least 90 percent, sequence identity to the VH sequence according to SEQ ID NO: 13; or (iii) a VL domain exhibiting at least 60, 70, 80, 90, 91, 92, 93, 94, 95, 96, 97, 98 or 99 percent, preferably at least 90 percent, sequence identity to the VL sequence according to SEQ ID NO: 14, and a VH domain exhibiting at least 60, 70, 80, 90, 91, 92, 93, 94, 95, 96, 97, 98 or 99 percent, preferably at least 90 percent, sequence identity to the VH sequence according to SEQ ID NO: 15.

In a more particular embodiment, said cognate pair of variable domains with specificity for human serum albumin comprises
  (i) a VL domain exhibiting at least 60, 70, 80, 90, 91, 92, 93, 94, 95, 96, 97, 98 or 99 percent, preferably at least 90 percent, sequence identity to the VL sequence according to SEQ ID NO: 10, wherein said VL domain comprises CDR domains CDR1, CDR2 and CDR3 taken from the VL sequence according to SEQ ID NO: 10, and a VH domain exhibiting at least 60, 70, 80, 90, 91, 92, 93, 94, 95, 96, 97, 98 or 99 percent, preferably at least 90 percent, sequence identity to VH sequence according to SEQ ID NO: 11, wherein said VH domain comprises CDR domains CDR1, CDR2 and CDR3 taken from the VH sequence according to SEQ ID NO: 11; or
  (ii) a VL domain exhibiting at least 60, 70, 80, 90, 91, 92, 93, 94, 95, 96, 97, 98 or 99 percent, preferably at least 90 percent, sequence identity to the VL sequence according to SEQ ID NO: 12, wherein said VL domain comprises CDR domains CDR1, CDR2 and CDR3 taken from the VL sequence according to SEQ ID NO: 12, and a VH domain exhibiting at least 60, 70, 80, 90, 91, 92, 93, 94, 95, 96, 97, 98 or 99 percent, preferably at least 90 percent, sequence identity to the VH sequence according to SEQ ID NO: 13, wherein said VH domain comprises CDR domains CDR1, CDR2 and CDR3 taken from the VH sequence according to SEQ ID NO: 13, preferably wherein said VL domain comprises K50Q and A51P (AHo numbering) and said VH domain comprises W54Y, V103T and Y105F (AHo numbering).

In a more particular embodiment, said cognate pair of variable domains with specificity for human serum albumin comprises a VL domain exhibiting at least 60, 70, 80, 90, 91, 92, 93, 94, 95, 96, 97, 98 or 99 percent, preferably at least 90 percent, sequence identity to the VL sequence according to SEQ ID NO: 14, wherein said VL domain comprises CDR domains CDR1, CDR2 and CDR3 taken from the VL sequence according to SEQ ID NO: 14, and a VH domain exhibiting at least 60, 70, 80, 90, 91, 92, 93, 94, 95, 96, 97, 98 or 99 percent, preferably at least 90 percent, sequence identity to the VH sequence according to SEQ ID NO: 15, wherein said VH domain comprises CDR domains CDR1, CDR2 and CDR3 taken from the VH sequence according to SEQ ID NO: 15, preferably wherein said VL domain comprises I2V, Q3V, K50Q and A51P (AHo numbering) and said VH domain comprises I55V, V103T, Y105F (AHo numbering).

In particular embodiments, said cognate pair of variable domains with specificity for human serum albumin comprises a VL domain comprising at least positions 5 to 140, particularly at least positions 3 to 145, of a protein sequence selected from SEQ ID NOs: 10, 12, and 14, and a VH domain comprising at least positions 5 to 140, particularly at least positions 3 to 145, of a protein sequence selected from SEQ ID NOs: 11, 13, and 15 (positions according to Honegger & Pluckthun, loc. cit.), particularly wherein said cognate pair of variable domains with specificity for human serum albumin comprises a VL domain selected from SEQ ID NOs: 10, 12, and 14, and a VH domain selected from SEQ ID NOs: 10, 12, and 14.

In particular embodiments, said cognate pair of variable domains with specificity for human CD3 comprises the three VL CDRs present in one of the VL protein sequence selected from SEQ ID NOs: 2, 4, 6 and 8 in a human antibody VL framework, wherein the VL framework comprises $V_K$ frameworks FR1, FR2 and FR3, particularly $V_K1$ frameworks, and a framework FR4, which is selected from a $V_K$ FR4, particularly $V_K1$ FR4, and a Vλ framework 4, and the three VH CDRs present in one of the VH protein sequences selected from SEQ ID NOs: 3, 5, 7 and 9 in a human antibody VH framework, particularly a VH3 framework.

In particular such embodiments, at least one of said VL domains comprises (i) human $V_K$ framework regions FR1 to FR3, particularly human $V_K1$ framework regions FR1 to FR3; (ii) CDR domains CDR1, CDR2 and CDR3; and (iii) a framework region IV, which is selected from
  a. a human Vλ germ line sequence for framework region IV, particularly a Vλ germ line sequence selected from the list of SEQ ID NO: 24 to 30 (SEQ ID NO. 16 to 22 according to WO 2014/206561);
  b. a Vλ-based sequence, which is (bi) a consensus Vλ sequence from human Vλ germ line sequences for framework region IV, particularly SEQ ID NO: 25 (SEQ ID NO. 17 according to WO 2014/206561); or (bii) a consensus Vλ sequence from rearranged human Vλ sequences for framework region IV, particularly a Vλ consensus sequence selected from the list of SEQ ID NO: 24 and 25 (SEQ ID NO. 16 and 17 according to WO 2014/206561); and
  c. a Vλ-based sequence, which has one or two mutations, particularly one mutation, compared to the closest human Vλ germ line sequence for framework region IV.

In a particular embodiment, said cognate pair of variable domains with specificity for human CD3 comprises (i) a VL domain exhibiting at least 60, 70, 80, 90, 91, 92, 93, 94, 95, 96, 97, 98 or 99 percent, preferably at least 90 percent, sequence identity to the VL sequence according to a sequence selected from SEQ ID NOs: 2, 4, 6 and 8, and/or (ii) a VH domain exhibiting at least 60, 70, 80, 90, 91, 92, 93, 94, 95, 96, 97, 98 or 99 percent, preferably at least 90 percent, sequence identity to the VH sequence according to a sequence selected from SEQ ID NOs: 3, 5, 7 and 9.

In a particular embodiment, said cognate pair of variable domains with specificity for human CD3 comprises (i) a VL domain exhibiting at least 60, 70, 80, 90, 91, 92, 93, 94, 95, 96, 97, 98 or 99 percent, preferably at least 90 percent, sequence identity to the VL sequence according to SEQ ID NO: 2, and a VH domain exhibiting at least 60, 70, 80, 90, 91, 92, 93, 94, 95, 96, 97, 98 or 99 percent, preferably at least 90 percent, sequence identity to the VH sequence according to SEQ ID NO: 3; or (ii) a VL domain exhibiting at least 60, 70, 80, 90, 91, 92, 93, 94, 95, 96, 97, 98 or 99 percent, preferably at least 90 percent, sequence identity to the VL sequence according to SEQ ID NO: 4, and a VH domain exhibiting at least 60, 70, 80, 90, 91, 92, 93, 94, 95, 96, 97, 98 or 99 percent, preferably at least 90 percent, sequence identity to the VH sequence according to SEQ ID NO: 5; or (iii) a VL domain exhibiting at least 60, 70, 80, 90, 91, 92, 93, 94, 95, 96, 97, 98 or 99 percent, preferably at least 90 percent, sequence identity to the VL sequence according to SEQ ID NO: 6, and a VH domain exhibiting at least 60, 70, 80, 90, 91, 92, 93, 94, 95, 96, 97, 98 or 99 percent, preferably at least 90 percent, sequence identity to the VH sequence according to SEQ ID NO: 7; or (iv) a VL domain exhibiting at least 60, 70, 80, 90, 91, 92, 93, 94, 95, 96, 97, 98 or 99 percent, preferably at least 90 percent, sequence identity to the VL sequence according to SEQ ID NO: 8, and a VH domain exhibiting at least 60, 70, 80, 90, 91, 92, 93, 94, 95, 96, 97, 98 or 99 percent, preferably at least 90 percent, sequence identity to the VH sequence according to SEQ ID NO: 9.

In a more particular embodiment, said cognate pair of variable domains with specificity for human CD3 comprises (i) a VL domain exhibiting at least 60, 70, 80, 90, 91, 92, 93, 94, 95, 96, 97, 98 or 99 percent, preferably at least 90 percent, sequence identity to the VL sequence according to SEQ ID NO: 2, wherein said VL domain comprises CDR domains CDR1, CDR2 and CDR3 taken from the VL sequence according to SEQ ID NO: 2, and a VH domain exhibiting at least 60, 70, 80, 90, 91, 92, 93, 94, 95, 96, 97, 98 or 99 percent, preferably at least 90 percent, sequence identity to the VH sequence according to SEQ ID NO: 3, wherein said VH domain comprises CDR domains CDR1, CDR2 and CDR3 taken from the VH sequence according to SEQ ID NO: 3; preferably wherein said VL domain comprises Y44F, K50Q, A51S and L54R (AHo numbering) and said VH domain comprises E53A, V103T and Y105F (AHo numbering), or (ii) a VL domain exhibiting at least 60, 70, 80, 90, 91, 92, 93, 94, 95, 96, 97, 98 or 99 percent, preferably at least 90 percent, sequence identity to the VL sequence according to SEQ ID NO: 4, wherein said VL domain comprises CDR domains CDR1, CDR2 and CDR3 taken from the VL sequence according to SEQ ID NO: 4, and a VH domain exhibiting at least 60, 70, 80, 90, 91, 92, 93, 94, 95, 96, 97, 98 or 99 percent, preferably at least 90 percent, sequence identity to the VH sequence according to SEQ ID NO: 5, wherein said VH domain comprises CDR domains CDR1, CDR2 and CDR3 taken from the VH sequence according to SEQ ID NO: 5; preferably wherein said VL domain comprises Y44F, K50Q, A51S and L54R (AHo numbering) and said VH domain comprises E53A, V103T and Y105F (AHo numbering), or (iii) a VL domain exhibiting at least 60, 70, 80, 90, 91, 92, 93, 94, 95, 96, 97, 98 or 99 percent, preferably at least 90 percent, sequence identity to the VL sequence according to SEQ ID NO: 6, wherein said VL domain comprises CDR domains CDR1, CDR2 and CDR3 taken from the VL sequence according to SEQ ID NO: 6, and a VH domain exhibiting at least 60, 70, 80, 90, 91, 92, 93, 94, 95, 96, 97, 98 or 99 percent, preferably at least 90 percent, sequence identity to the VH sequence according to SEQ ID NO: 7, wherein said VH domain comprises CDR domains CDR1, CDR2 and CDR3 taken from the VH sequence according to SEQ ID NO: 7; or (iv) a VL domain exhibiting at least 60, 70, 80, 90, 91, 92, 93, 94, 95, 96, 97, 98 or 99 percent, preferably at least 90 percent, sequence identity to the VL sequence according to SEQ ID NO: 8, wherein said VL domain comprises CDR domains CDR1, CDR2 and CDR3 taken from the VL sequence according to SEQ ID NO: 8, and a VH domain exhibiting at least 60, 70, 80, 90, 91, 92, 93, 94, 95, 96, 97, 98 or 99 percent, preferably at least 90 percent, sequence identity to the VH sequence according to SEQ ID NO: 9, wherein said VH domain comprises CDR domains CDR1, CDR2 and CDR3 taken from the VH sequence according to SEQ ID NO: 9.

In particular embodiments, said cognate pair of variable domains with specificity for human CD3 comprises a VL domain comprising at least positions 5 to 140, particularly at least positions 3 to 145, of a protein sequence selected from SEQ ID NOs: 2, 4, 6 and 8, and a VH domain comprising at least positions 5 to 140, particularly at least positions 3 to 145, of a protein sequence selected from SEQ ID NOs: 3, 5, 7 and 9 (positions according to Honegger & Pluckthun, loc. cit.), particularly wherein said cognate pair of variable domains with specificity for human CD3 comprises a VL domain selected from SEQ ID NOs: 2, 4, 6 and 8, and a VH domain selected from SEQ ID NOs: 3, 5, 7 and 9.

In particular such embodiments, said third, fourth, fifth and/or sixth binding domains are single-chain Fv fragments with specificity for a target selected from the list of: a cancer target, and a target present on immune effector cells.

In the context of the present application the term "target" refers to a cognate binding partner of a binding domain, such as an antigen of an antibody that is specifically bound by such binding domain.

In particular embodiments, said target is a cancer target, in particular an antigen or an epitope that is present on the surface of one or more tumour cell types or tumour-associated cells in an increased concentration and/or in a different steric configuration as compared to the surface of non-tumour cells. Particularly, said cancer target is present on the surface of one or more tumour or tumour stroma cell types, but not on the surface of non-tumour cells.

In other particular embodiments, said target is an antigen or epitope that is preferentially expressed on cells involved in autoimmune diseases. In other embodiments, said antigen or epitope is preferentially expressed on cells involved in an inflammatory disease.

In certain embodiments, said first and said second single-chain protein are selected from the following list, wherein VLA, VLB, VHA, and VHB correspond to said first and second VL and VH domains, respectively, and VLC, VLD, VLE, VLF, VHC, VHD, VHE, and VHF are part of single-chain fragments with a linker corresponding to said third, fourth, fifth and/or sixth functional domain, respectively, linked via third, fourth, fifth and/or sixth linkers LINKER3, LINKER4, LINKER5 and LINKER6) to the core domain (in bold letters); all constructs are written in the direction N- to C-terminus:

A (Parallel; 6Fvs):
    chain 1: VLC-(linker)-VHC-(LINKER3)-VLA-(LINKER1)-VLB-(LINKER4)-VLD-(linker)-VHD
    chain 2: VLE-(linker)-VHE-(LINKER5)-VHA-(LINKER2)-VHB-(LINKER6)-VLF-(linker)-VHF B (Anti-Parallel 6Fvs):
    chain 1: VLC-(linker)-VHC-(LINKER3)-VLA-(LINKER1)-VLB-(LINKER4)-VLD-(linker)-VHD
    chain 2: VLE-(linker)-VHE-(LINKER5)-VHB-(LINKER2)-VHA-(LINKER6)-VLF-(linker)-VHF C1 (Anti-Parallel 4 Fvs) (See FIG. 12):
    chain 1: VLC-(linker)-VHC-(LINKER3)-VLA-(LINKER1)-VLB
    chain 2: VLD-(linker)-VHD-(LINKER4)-VHB-(LINKER2)-VHA

C2 (Anti-Parallel 4 Fvs) (See FIG. 14):
    chain 1: VLC-(linker)-VHC-(LINKER3)-VLA-(LINKER1)-VLB
    chain 2: VHB-(LINKER2)-VHA-(LINKER4)-VLD-(linker)-VHD C3 (Anti-Parallel 4 Fvs):
  chain 1: VLA-(LINKER1)-VLB-(LINKER3)-VLC-(linker)-VHC
  chain 2: VLD-(linker)-VHD-(LINKER4)-VHB-(LINKER2)-VHA
C4 (Anti-Parallel 4 Fvs):
  chain 1: VLA-(LINKER1)-VLB-(LINKER3)-VLC-(linker)-VHC
  chain 2: VHB-(LINKER2)-VHA-(LINKER4)-VLD-(linker)-VHD
D1 (Parallel 4 Fvs) (See FIG. 15):
  chain 1: VLC-(linker)-VHC-(LINKER3)-VLA-(LINKER1)-VLB
  chain 2: VLD-(linker)-VHD-(LINKER4)-VHA-(LINKER2)-VHB
D2 (Parallel 4 Fvs):
  chain 1: VLC-(linker)-VHC-(LINKER3)-VLA-(LINKER1)-VLB
  chain 2: VHA-(LINKER2)-VHB-(LINKER4)-VLD-(linker)-VHD
D3 (Parallel 4 Fvs):
  chain 1: VLA-(LINKER1)-VLB-(LINKER3)-VLC-(linker)-VHC
  chain 2: VLD-(linker)-VHD-(LINKER4)-VHA-(LINKER2)-VHB
D4 (Parallel 4 Fvs):
  chain 1: VLA-(LINKER1)-VLB-(LINKER3)-VLC-(linker)-VHC
  chain 2: VHA-(LINKER2)-VHB-(LINKER4)-VLD-(linker)-VHD In certain embodiments, the order of the VH and VL domains in one or more of the scFv fragments comprised in the constructs according to the heterodimeric formats A, B, C1 to C4, or D1 to D4 are in the reverse order (e.g. VHC-(linker)-VLC-(LINKER3)-VLA-(LINKER1)-VLB-(LINKER4)-VHD-(linker)-VLD in chain 1 of construct A).

In these formats the localization of two split variable heavy domains VHA and VHB on one protein chain and the two corresponding variable light domains VLA and VLB on the other protein chain (VH-VH/VL-VL) prevents the formation of intra-chain domain pairings resulting in inactive single-chain diabody (scDb)-like structures as it would be the case if the VH-VL/VH-VL orientation of the conventional diabody—similar to the design suggested by Kipriyanov et al—had been used to drive hetero-dimerization. In contrast, the VH-VH/VL-VL-orientation forces the formation of exclusively hetero-dimeric bi- to hexa-specific proteins.

There is the theoretical possibility that the VH/VL domain pairing of the target A and B binding VHA-VHB/VLA-VLB core domain would result in an inactive core domain due to the inappropriate pairing of VHA with VLB and VHB with VLA resulting in VHA-VLB and VHB-VLA pairs. Unexpectedly and surprisingly, such inactive variants have not been observed so far. Without wishing to be bound by theory, dimerization could be driven towards cognate pairing due to the more efficient packing of the CDRs of cognate pairs as opposed to potential packing interferences occurring in non-matching pairings.

In order to further drive the hetero-dimerization towards active pairing in the VH-VH/VL-VL core domain, the knob-into-hole or similar technologies could be applied in one or—if reciprocally applied—both VL/VH pairs of the VH-VH/VL-VL core domain. Thus, in certain embodiments, the active pairing in the VH-VH/VL-VL core domain of said hetero-dimeric protein is further supported by a technology selected from: knob-into-hole (Zhu et al., "Remodeling domain interfaces to enhance heterodimer formation", Protein Sci 1997 Apr.; 6(4): 781-788.), and inter-chain cysteine bridges.

In a second aspect, the present invention relates to one or two nucleic acid sequences encoding said first and a second single-chain proteins.

In a third aspect, the present invention relates to one or two vectors comprising said one or two nucleic acid sequences.

In a fourth aspect, the present invention relates to a host cell or host cells comprising said one or two vectors.

In a fourth aspect, the present invention relates to a method for producing the first and second single-chain proteins, or the hetero-dimeric protein, of the present invention, comprising (i) providing a nucleic acid or nucleic acids according to the present invention, or a vector or vectors according to the present invention, expressing said nucleic acid or nucleic acids or said vector or vectors and collecting said first and second single-chain proteins, or said hetero-dimeric protein, from the expression system, or (ii) providing a host cell or host cells of the present invention, culturing said host cell or host cells, and collecting said first and second single-chain proteins, or said hetero-dimeric protein, from the cell culture.

In a fifth aspect, the present invention relates to a pharmaceutical composition comprising the hetero-dimeric protein of the present invention and a pharmaceutically acceptable carrier. Pharmaceutically acceptable carriers enhance or stabilize the composition, or facilitate preparation of the composition. Pharmaceutically acceptable carriers include solvents, dispersion media, coatings, antibacterial and antifungal agents, isotonic and absorption delaying agents, and the like that are physiologically compatible.

In a sixth aspect, the present invention relates to the hetero-dimeric protein of the present invention for use in the treatment of a disease, particularly a human disease, more particularly a human disease selected from cancer, an inflammatory and an autoimmune disease. In particular embodiments, at least one of said third, fourth, fifth, or sixth functional domain is able to specifically interact with a target of therapeutic relevance in the corresponding disease.

The terms "treatment", "treating", "treat", "treated", and the like, as used herein, refer to obtaining a desired pharmacologic and/or physiologic effect. The effect may be therapeutic in terms of a partial or complete cure for a disease and/or adverse effect attributable to the disease or delaying the disease progression. "Treatment", as used herein, covers any treatment of a disease in a mammal, e.g., in a human, and includes: (a) inhibiting the disease, e.g., arresting its development; and (c) relieving the disease, e.g., causing regression of the disease.

In a seventh aspect the present invention relates to a method for the treatment of a disease, particularly a human disease, more particularly a human disease selected from cancer, an inflammatory and an autoimmune disease, comprising the step of administering the hetero-dimeric protein of the present invention, wherein at least one of said third, fourth, fifth, or sixth functional domains is able to specifically interact with a target of therapeutic relevance in the corresponding disease. In particular, the present invention relates to a method for treating a subject suffering from a disease selected from cancer, an inflammatory and an autoimmune disease, comprising administering to said subject an effective amount of the hetero-dimeric protein of the present invention, wherein at least one of said third, fourth, fifth, or sixth functional domain is able to specifically interact with a target of therapeutic relevance in the corresponding disease.

The term "subject" includes human and non-human animals. Non-human animals include all vertebrates, e.g., mammals and non-mammals, such as non-human primates, sheep, dog, cow, chickens, amphibians, and reptiles. Except when noted the terms "patient" or "subject" are used herein interchangeably.

The term "effective amount" or "therapeutically effective amount" or "efficacious amount" refers to the amount of an agent that, when administered to a mammal or other subject for treating a disease, is sufficient to effect such treatment for the disease. The "therapeutically effective amount" will vary depending on the agent, the disease and its severity and the age, weight, etc., of the subject to be treated.

In an eights aspect the present invention relates to use of the hetero-dimeric protein of the present invention in a manufacture of a medicament for use in the treatment of a disease, particularly a human disease, more particularly a human disease selected from cancer, an inflammatory and an autoimmune disease, wherein at least one of said cognate pairs of VL and VH domains, or of said third, fourth, fifth, or sixth functional domain is able to specifically interact with a target of therapeutic relevance in the corresponding disease.

In a ninth aspect the present invention relates to use of the hetero-dimeric protein of the present invention in the treatment of a disease, particularly a human disease, more particularly a human disease selected from cancer, an inflammatory and an autoimmune disease, wherein at least one of said cognate pairs of VL and VH domains, or of said third, fourth, fifth, or sixth functional domain is able to specifically interact with a target of therapeutic relevance in the corresponding disease.

LITERATURE

R1. Skerra, A., and Plückthun, A. (1988). Assembly of a functional immunoglobulin Fv fragment in *Escherichia coli*. Science 240, 1038-1041.

R2. Röthlisberger et al., (2005). Domain interactions in the Fab fragment: A comparative evaluation of the single-chain Fv and Fab format engineered with variable domains of different stability. J Mol Biol 347, 773-789.

R3. Ridgway et al., 1996. 'Knobs-into-holes' engineering of antibody CH3 domains for heavy chain heterodimerization. Protein Eng. 9, 617-621.

R4. Zhu (1997) Remodeling domain interfaces to enhance heterodimer formation. Protein Sci. 6, 781-788

R5. Schaefer, W., et al., 2011b. Immunoglobulin domain crossover as a generic approach for the production of bispecific IgG antibodies. Proc. Natl. Acad. Sci. U.S.A. 108, 11187-11192.

R6. Holliger et al., "Diabodies": small bivalent and bispecific antibody fragments. Proc. Natl. Acad. Sci. U.S.A. 90, 6444-6448.

R7. Arndt et al., 1999. A bispecific diabody that mediates natural killer cell cytotoxicity against xeno-transplanted human Hodgkin's tumors. Blood 94, 2562-2568.

R8. Kipriyanov et al., 1999. Bispecific tandem diabody for tumor therapy with improved antigen binding and pharmacokinetics. J. Mol. Biol. 293, 41-56.

R9. Alt et al., 1999. Novel tetravalent and bispecific IgG-like antibody molecules combining single-chain diabodies with the immunoglobulin gamma1 Fc or CH3 region. FEBS Lett. 454, 90-94.

R10. Johnson et al., 2010. Effector cell recruitment with novel Fv-based dual-affinity retargeting protein leads to potent tumor cytolysis and in vivo B-cell depletion. J. Mol. Biol. 399, 436-449.

R11. De Jonge et al., (1995) Production and characterization of bispecific single-chain antibody fragments. Mol. Immunol. 32, 1405-1412.

R12. Reiter et al., (1994) Engineering interchain disulfide bonds into conserved framework regions of Fv fragments: improved biochemical characteristics of recombinant immunotoxins containing disulfide-stabilized Fv. Protein Eng. 7, 697-704.

R13. Pack, P., and Pluckthun, A. (1992). Miniantibodies: Use of amphipathic helices to produce functional, flexibly linked dimeric Fv fragments with high avidity in *Escherichia coli*. Biochemistry 31, 1579-1584.

R14. Schoonjans et al., Fab chains as an efficient heterodimerization scaffold for the production of recombinant bispecific and trispecific antibody derivatives. J Immunol. 2000 Dec. 15; 165(12):7050-7.

R15. Orcutt et al., 2009. A modular IgG-scFv bispecific antibody topology. Pro-tein Eng. Des. Sel. 23, 221-228.

R16. Wu, C. et al., 2007. Simultaneous targeting of multiple disease mediators by a dual-variable-domain immunoglobulin. Nat. Biotechnol. 25, 1290-1297.

R17. "mAbs"; Köhler & Milstein, Nature. 256 (1975) 495-7

R18. Umaña et al., 1999. Engineered glycoforms of an antineuroblastoma IgG1 with optimized antibody-dependent cellular cytotoxic activity. Nat. Biotechnol. 17, 176-180

R19. Yu, Y. J. et al. Sci. Trans. Med. 3, 84ra44 (2011).

R20. Hinton P R. et al., 2004. Engineered human IgG antibodies with longer serum half-lives in primates. J Biol Chem. 279(8):6213-6.

R21. Spiess et al., 2015. Alternative molecular formats and therapeutic applications for bispecific antibodies. Mol Immunol. 2015 Jan. 27.

R22. Davis et al., 2013. Readily isolated bispecific antibodies with native immunoglobulin format. U.S. Pat. No. 8,586,713. Regeneron Pharmaceuticals, Inc.

R23. Shahied L S, et al., Bispecific minibodies targeting HER2/neu and CD16 exhibit improved tumor lysis when placed in a divalent tumor antigen binding format. J Biol Chem. 2004 Dec. 24; 279(52):53907-14. Epub 2004 Oct. 7.

R24. Milstein. C and Cuello. A. C. (1983) Nature, 305, 537-54

R25. Chang et al., The dock and lock method: a novel platform technology for building multivalent, multifunctional structures of defined composition with retained bioactivity. Clin Cancer Res. 2007 Sep. 15; 13(18 Pt 2):5586s-5591s.

R26. Deyev et al., (2003). Design of multivalent complexes using the barnase-barstar module. Nature biotechnology, 21(12), 1486-1492.

R27. Pack, P., and Pluckthun, A. (1992). Miniantibodies: Use of amphipathic helices to produce functional, flexibly linked dimeric Fv fragments with high avidity in *Escherichia coli*. Biochemistry 31, 1579-1584.

R28. Halin et al. (2003). Synergistic therapeutic effects of a tumor targeting antibody fragment, fused to interleukin 12 and to tumor necrosis factor α. Cancer research, 63(12), 3202-3210.

R29. D. Müller et al., Improved pharmacokinetics of recombinant bispecific antibody molecules by fusion to human serum albumin J. Biol. Chem., 282 (2007), pp. 12650-12660

R30. EP1293514
R31. Milstein C, and Cuello A C (1983) Hybrid hybridomas and their use in immunohistochemistry. Nature 305:537-540
R32. Eskander R N, Tewari K S: Epithelial cell-adhesion molecule directed trifunctional antibody immunotherapy for symptom management of advanced ovarian cancer. Clin Pharmacol 2013, 5:55-61.
R33. Stieglmaier J, Benjamin J, Nagorsen D: Utilizing the BiTE (bispecific T-cell engager) platform for immunotherapy of cancer. Expert Opin Biol Ther 2015, 15:1093-1099.
R34. Bluemel C, Hausmann S, Fluhr P, Sriskandarajah M, Stallcup W B, Baeuerle P A, Kufer P: Epitope distance to the target cell membrane and antigen size determine the potency of T cell mediated lysis by BiTE antibodies specific for a large melanoma surface antigen. Cancer Immunol Immunother 2010, 59:1197-1209.
R35. Köhnke T, Krupka C, Tischer J, Kno"sel T, Subklewe M: Increase of PD-L1 expressing B-precursor ALL cells in a patient resistant to the CD19/CD3-bispecific T cell engager antibody blinatumomab. J Hematol Oncol 2015, 8:111.
R36. Junttila T T, Li J, Johnston J, Hristopoulos M, Clark R, Ellerman D, Wang B E, Li Y, Mathieu M, Li G: Antitumor efficacy of a bispecific antibody that targets HER2 and activates T cells. Cancer Res 2014, 74:5561-5571.
R37. Laszlo G S, Gudgeon C J, Harrington K H, Walter R B: T-cell ligands modulate the cytolytic activity of the CD33/CD3 BiTE antibody construct, AMG 330. Blood Cancer J 2015, 5:e340.
R38. Arndt C, Feldmann A, von Bonin M, Cartellieri M, Ewen E, Koristka S, Michalk I, Stamova S, Berndt N, Gocht A et al.: Costimulation improves the killing capability of T cells redirected to tumor cells expressing low levels of CD33: description of a novel modular targeting system. Leukemia 2014, 28:59-69.
R39. Compte M, Alvarez-Cienfuegos A, Nuñez-Prado N, et al. Functional comparison of single-chain and two-chain anti-CD3-based bispecific antibodies in gene immunotherapy applications. Oncoimmunology. 2014;3:e28810. doi:10.4161/onci.28810.
R40. Yariv Mazor, Kris F. Sachsenmeier, Chunning Yang, Anna Hansen, Jessica Filderman, Kathy Mulgrew, Herren Wu & William F. Dall'Acqua; Enhanced tumor-targeting selectivity by modulating bispecific antibody binding affinity and format valence. Scientific Reports 7, Article number: 40098 (2017) doi:10.1038/srep40098
R41. Reiter Y, Brinkmann U, Lee B, Pastan I., Engineering antibody Fv fragments for cancer detection and therapy: disulfide-stabilized Fv fragments. Nat Biotechnol. 1996 October;14(10):1239-45.

EXAMPLES

Example 1: Construction of Multispecific Formats

Methods and Results

Construct Design, Expression and Purification

The heterodimeric MATCH molecules were designed to contain the specificity for CD3ε and HSA in the split-variable domains of the heterodimeric core assembly. An IL23R binding scFv was attached to the N-terminus of each of the heterodimerization domains. In order covalently associate the two peptide chains of the MATCH and to confirm the correct assembly of the corresponding domains in the heterodimerization core an interchain disulfide (described in [11]) was introduced in the VL/VH interface of either the anti-CD3 or the anti-HSA domain.

A number of different embodiments were generated varying parameters like, MATCH arrangement (parallel or anti-parallel), CD3 binding domains used (clones 28-21-D09 or 09-24-H09), HSA binding domain used (clones 19-01-H04 or 23-13-A01) and different core linkers (SEQ 16-20). The two possible arrangements (parallel or anti-parallel) of the MATCH format have been described in detail (WO2016202457) the antiparallel arrangement (ap): Chain A (VL1-VH1-VH2-VH3) and Chain B (VL4-VH4-VL3-VL2); and the parallel arrangement (p): Chain A (VL1-VH1-VH2-VH3) and Chain B (VL4-VH4-VL2-VL3). Other than the variation of the arrangement also different choices for the core domains, the scFv modules and core linkers shown in Tables 1 and 2 have been tested:

TABLE 1

Sequence listings, CDR residues highlighted in bold

| Sequence ID (SEQ ID) | Description | Sequence |
|---|---|---|
| 1 | Anti-IL23R scFv module 14-11-D07 | DIQMTQSPSSLSASVGDRVTITCQASENIYSFLAWYQQKPGKAPKLLIYSASKLAAGVPSRFSGSGSGTDFTLTISSLQPEDFATYYCQQTNRYSNPDIYNVFGTGTKVTVL G ggggsggggsggggsggggs EVQLVESGGGLVQPGGSLRLSCAASGIDFNSNYYMCWVRQAPGKGLEWIGCIYVGSHVNTYYANWAKGRFTISRDNSKNTVYLQMNSLRAEDTAVYYCATSGSSVLYFKFWGQGTLVTVSS ggggsggggs |
| 2 | Anti-CD3 VL 28-21-D09-sc04 diS | DIQMTQSPSSLSASVGDRVTITCQSSQSVFSNNYLAWFQQKPGQSPKRLIYSASTLASGVPSRFSGSGSGTDFTLTISSLQPEDFATYYCLGSYACSSADCYVFGCGTKVTVLG |
| 3 | Anti-CD3 VH 28-21-D09-sc04 diS | EVQLVESGGGLVQPGGSLRLSCAASGFSLSSYDMSWVRQAPGKCLAWIGASYASGPTYYASWAKGRFTISRDNSKNTVYLQMNSLRAEDTATYFCARGGWTGTSHSNIWGQGTLVTVSS |
| 4 | Anti-CD3 VL 28-21-D09-sc04 | DIQMTQSPSSLSASVGDRVTITCQSSQSVFSNNYLAWFQQKPGQSPKRLIYSASTLASGVPSRFSGSGSGTDFTLTISSLQPEDFATYYCLGSYACSSADCYVFGTGTKVTVLG |

TABLE 1-continued

Sequence listings, CDR residues highlighted in bold

| Sequence ID (SEQ ID) | Description | Sequence |
|---|---|---|
| 5 | Anti-CD3 VH 28-21-D09-sc04 | EVQLVESGGGLVQPGGSLRLSCAASGFSLSSYDMSWVRQAPGKGLAWIGASYA SGPTYYASWAKGRFTISRDNSKNTVYLQMNSLRAEDTATYFCARGGWTGTSHSN IWGQGTLVTVSS |
| 6 | Anti-CD3 VL 09-24-H09-sc10 diS | Diqmtqspsslsasvgdrvtitcqssesvynnkrlswyqqkpgkapklliytasslas gvpsrfsgsgsgtdftltisslqpedfatyycqgeftcsnadcftfgCgtkvtvlg |
| 7 | Anti-CD3 VH 09-24-H09-sc10 diS | evqlvesggglvqpggslrlscaasgflssyamiwvrqapgkClewigmilragniyyasw vkgrftisrdnskntvylqmnslraedtavyycarrhynregypigigdlwgqgtlvtvss |
| 8 | Anti-CD3 VL 09-24-H09-sc10 | Diqmtqspsslsasvgdrvtitcqssesvynnkrlswyqqkpgkapklliytassl asgvpsrfsgsgsgtdftltisslqpedfatyycqgeftcsnadcftfgtgtkvtvlg |
| 9 | Anti-CD3 VH 09-24-H09-sc10 | evqlvesggglvqpggslrlscaasgflssyamiwvrqapgkglewigmilragniyya swykgrftisrdnskntvylqmnslraedtavyycarrhynregypigigdlwgqgtlvt vss |
| 10 | Anti-HSA VL 19-01-H04-sc03 | DIQMTQSPSSLSASVGDRVTITCQSSESVYSNNQLSWYQQKPGQPPKLLIYDASD LASGVPSRFSGSGSGTDFTLTISSLQPEDFATYYCAGGFSSSSDTAFGGGTKLTV LG |
| 11 | Anti-HSA VH 19-01-H04-sc03 | EVQLVESGGGLVQPGGSLRLSCAASGFSLSSNAMGWVRQAPGKGLEYIGIISVG GFTYYASWAKGRFTISRDNSKNTVYLQMNSLRAEDTATYFCARDRHGGDSSGAF YLWGQGTLVTVSS |
| 12 | Anti-HSA VL 19-01-H04-sc03-Cys | DIQMTQSPSSLSASVGDRVTITCQSSESVYSNNQLSWYQQKPGQPPKLLIYDASD LASGVPSRFSGSGSGTDFTLTISSLQPEDFATYYCAGGFSSSSDTAFGCGTKLTV LG |
| 13 | Anti-HSA VH 19-01-H04-sc03-Cys | EVQLVESGGGLVQPGGSLRLSCAASGFSLSSNAMGWVRQAPGKCLEYIGIISVGG FTYYASWAKGRFTISRDNSKNTVYLQMNSLRAEDTATYFCARDRHGGDSSGAFY LWGQGTLVTVSS |
| 14 | Anti-HSA VL 23-13-A01-sc02 | DVVMTQSPSSLSASVGDRVTITCQASQIISSRSAWYQQKPGQPPKLLIYQASKLA SGVPSRFSGSGSGTDFTLTISSLQPEDFATYYCQCTYIDSNFGAFGGGTKLTVLG |
| 15 | Anti-HSA VH 23-13-A01-sc02 | EVQLVESGGGLVQPGGSLRLSCAASGFSFSSSYWICWVRQAPGKGLEWVGCVF TGDGTTYYASWAKGRFTISRDNSKNTVYLQMNSLRAEDTATYFCARPVSVYYYG MDLWGQGTLVTVSS |
| 16 | Core Linker 1A | epepepepepepep |
| 17 | Core Linker 1B | kpkpkpkpkpkpkp |
| 18 | Core Linker 2 | sggggsggggs |
| 19 | Core Linker 3 | ggggsggggsggggs |
| 20 | Core Linker 4 | aeaaakeaaaka |
| 21 | Anti-Her2 scFv module | DIQMTQSPSSLSASVGDRVTITCRASQDVNTAVAWYQQKPGKAPKLLIYSASFLY SGVPSRFSGSRSGTDFTLTISSLQPEDFATYYCQQHYTTPPTFGGGTKLTVLG ggggsggggsggggsggggs EVQLVESGGGLVQPGGSLRLSCAASGFNIKDTYIHWVRQAPGKGLEWVARIYPTN GYTRYADSVKGRFTISADTSKNTAYLQMNSLRAEDTAVYYCSRWGGDGFYAMDY WGQGTLVTVSS ggggsggggs |
| 22 | PRO746 Chain A | diqmtqspsslsasvgdrvtitcqaseniysflawyqqkpgkapklliysasklaagvpsrfs gsgsgtdftltisslqpedfatyycqqtnrysnpdiynvfgtgtkvtvlgggggsggggsggg gsggggsevqlvesggglvqpggslrlscaasgidfnsyymcwvrqapgkglewigciyvgs hvntyyanwakgrftisrdnskntvylqmnslraedtavyycatsgssvlyfkfwgqgtlvtv ssggggsggggsdiqmtqspsslsasvgdrvtitcqssqsvfsnnylawfqqkpgqspkrliy |

TABLE 1-continued

Sequence listings, CDR residues highlighted in bold

| Sequence ID (SEQ ID) | Description | Sequence |
|---|---|---|
|  |  | sastlasgvpsrfsgsgsgtdftltisslqpedfatyyclgsyacssadcyvfgcgtkvtvlg epepepepepepepdiqmtqspsslsasvgdrvtitcqssesvysnnqlswyqqkpgqppkll iydasdlasgvpsrfsgsgsgtdftltisslqpedfatyycaggfssssdtafgggtkltvlg |
| 23 | PRO746 Chain B | diqmtqspsslsasvgdrvtitcqaseniysflawyqqkpgkapklliysasklaagvpsrfs gsgsgtdftltisslqpedfatyycqqtnrysnpdiynvfgtgtkvtvlgggggsggggsggg gsggggsevqlvesgggglvqpggslrlscaasgidfnsnyymcwvrqapgkglewigciyvgs hvntyyanwakgrftisrdnskntvylqmnslraedtavyycatsgssvlyfkfwgqgtlvtv ssgggggsggggsevqlvesgggglvqpggslrlscaasgfslssnamgwvrqapgkgleyigii svggftyyaswakgrftisrdnskntvylqmnslraedtatyfcardrhggdssgafylwgqg tlvtvsskpkpkpkpkpkpkpevqlvesgggglvqpggslrlscaasgfslssydmswvrqapg kclawigasyasgptyyaswakgrftisrdnskntvylqmnslraedtatyfcarggwtgtsh sniwgqgtlvtvss |
| 24 | Vλ germline-based FR4 | FGTGTKVTVLG |
| 25 | Vλ germline-based FR4 | FGGGTKLTVLG |
| 26 | Vλ germline-based FR4 | FGGGTQLIILG |
| 27 | Vλ germline-based FR4 | FGEGTELTVLG |
| 28 | Vλ germline-based FR4 | FGSGTKVTVLG |
| 29 | Vλ germline-based FR4 | FGGGTQLTVLG |
| 30 | Vλ germline-based FR4 | FGGGTQLTALG |

TABLE 2

Construct overview, the combination of sequences listed from N- to C-terminus

| ID PRO | Chain | scFv module (SEQ ID) | Core domain (SEQ ID) | Core Linker (SEQ ID) | Core domain (SEQ ID) | Arrangement | Description |
|---|---|---|---|---|---|---|---|
| 746 | A | 1 | 2 | 16 | 10 | anti-parallel [ap] | diS in αCD3 domain, charged linker |
|  | B | 1 | 11 | 17 | 3 |  |  |
| 733 | A | 1 | 6 | 18 | 10 | Parallel [p] | diS in αCD3 domain, 11 aa GS-linker, alternative αCD3 |
|  | B | 1 | 7 | 18 | 11 |  |  |
| 734 | A | 1 | 2 | 18 | 10 | ap | diS in αCD3 domain, 11 aa GS-linker |
|  | B | 1 | 11 | 18 | 3 |  |  |
| 736 | A | 1 | 2 | 19 | 10 | p | diS in αCD3 domain, 15 aa GS-linker |
|  | B | 1 | 3 | 19 | 11 |  |  |
| 737 | A | 1 | 6 | 19 | 10 | p | diS in αCD3 domain, 15 aa GS-linker, alternative αCD3 |
|  | B | 1 | 7 | 19 | 11 |  |  |
| 738 | A | 1 | 2 | 19 | 10 | ap | diS in αCD3 domain, 15 aa GS-linker |
|  | B | 1 | 11 | 19 | 3 |  |  |
| 739 | A | 1 | 6 | 19 | 11 | ap | diS in αCD3 domain, 15 aa GS-linker, alternative αCD3 |
|  | B | 1 | 10 | 19 | 7 |  |  |
| 741 | A | 1 | 2 | 18 | 14 | ap | diS in αCD3 domain, 11 aa GS-linker, alternative αHSA |
|  | A | 1 | 15 | 18 | 3 |  |  |
| 747 | A | 1 | 2 | 20 | 10 | ap | diS in αCD3 domain, helical linker |
|  | B | 1 | 11 | 20 | 3 |  |  |
| 821 | A | 21 | 2 | 16 | 10 | ap | diS in αCD3 domain, charged linker, additional αHer2 |
|  | B | 1 | 11 | 17 | 3 |  |  |
| 824 | A | 1 | 4 | 16 | 12 | ap | diS in αHSA domain, charged linker, additional αHer2 |
|  | B | 21 | 13 | 17 | 5 |  |  |

To generate the constructs outlined in above the amino acid sequences for the Fv domains and linkers were back-translated into corresponding nucleic sequences, which were de novo synthesized. The coding sequences were assembled and cloned by standard molecular biology techniques (e.g. Sambrook, J., et al., Molecular Cloning: A Laboratory Manual) into a suitable expression vector (e.g. pcDNA3.1, Invitrogen) for recombinant protein secretion.

The MATCH protein was produced in CHO-S cells (Thermo Fisher) by transient transfection using CHOgro® expression kit (Mirus Bio® LLC) according to supplier's protocol. Protein fraction was purified from CHO-S supernatant which was harvested by centrifugation as soon as cell viability decreased below 80% (after 6 days of incubation with orbital shaking at 37° C. and 8% CO2). Purification was done by protein L-affinity purification, capturing variable domains with Capto® L resin (GE Healthcare) in a column affixed to an ÄKTA Pure® FPLC system (GE Healthcare) and eluted with 0.1 M Citric acid, pH 2.0, followed by the rapid adjustment of sample pH with the addition of ⅓ (v/v) 2M tris(hydroxymethyl)aminomethane hydrochloride (Tris™-HCl), pH 7.5. Protein solutions were then buffer exchanged with 1xPBS pH7.4 (supplemented with 300 mM Arginine) using a dialysis membrane (3.5 kDa MWCO, Spectrum Laboratories, Inc.) and finally concentrated using a Vivaspin® Protein Concentrator Spin Column (5 kDa MWCO, GE Healthcare).

The reference proteins in the single-chain diabody (scDb) format were designed as described previously [10]. In short, the variable domains as listed in Table 1 were arranged in an VLA-S1-VHB-L1-VLB-S2-VHA fashion, where S1 and S2 are short $GS_4$ linkers and L1 is a long $(GS_4)_4$ linker. The molecules generated for reference purposes included the identical Fv fragments as the MATCH construct.

All tested proteins were analyzed by size-exclusion high-performance liquid chromatography (SE-HPLC) and sodium dodecyl sulfate polyacrylamide gel electrophoresis (SDS-PAGE) for purity and UV/Vis spectroscopy for protein content. In case of the MATCH construct the quantitative disulfide linking of the two heterodimers was confirmed by non-reducing SDS-PAGE.

Results

Figure 1:
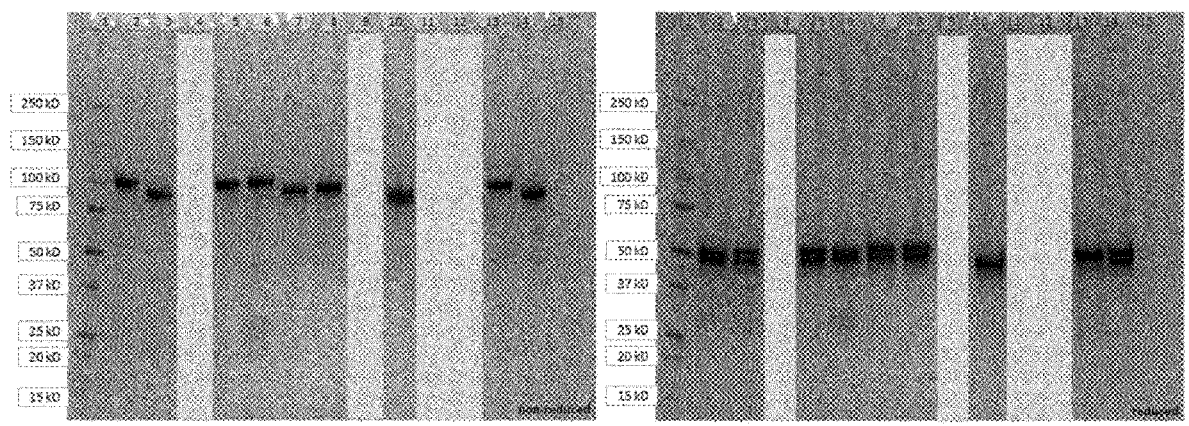
FIG. 1 shows the SDS-PAGE analysis of the MATCH construct variants described in Table 2 under reducing and non-reducing conditions.

The SDS-PAGE analysis of the MATCH construct variants shows in FIG. 1 that under non-reducing conditions a nearly quantitative shift of the protein band to the covalently linked heterodimer is observed. Under reducing conditions, however, a double-band at the size of the individual chains is observed.

→Due to the position of the designated interchain disulfide bridge in the interface of a VL/VH pair a mispairing of the chains is highly unlikely, especially in combination with the conserved affinity of the core domains in the SPR experiment Affinity Measurement by Surface Plasmon Resonance (SPR)

Binding affinities of individual target binding domains in the single-chain Fv (scFv) format as well as of the purified hetero-dimeric MATCH constructs to recombinant target proteins human IL-23 receptor ECD (IL23R), human CD3 gamma-epsilon single-chain (CD3) and human serum albumin (HSA) were measured by surface plasmon resonance (SPR) using a Biacore® T200 SPR apparatus (General Electric®) or a MASS-1 (Sierra Sensors®) device. In brief, recombinant proteins were directly immobilized by amine coupling chemistry on a CM5 (Biacore®, General Electric®) or high capacity sensor chip (Sierra Sensors®). Different concentrations of target binding domains were injected as analyte and the binding response (in response units, RU) was measured. After each injection regeneration procedure was performed. Obtained binding data were double-subtracted (zero analyte injection, reference flow channel) and analyzed using the respective software package.

Results

TABLE 3

| Affinity of hetero-dimeric MATCH construct | | | | |
| --- | --- | --- | --- | --- |
| Protein ID | Affinity to human CD3 [M] | Affinity to cyno CD3 [M] | Affinity to HSA [M] | Affinity to IL23R [M] |
| PRO325 (scFv) | Not applicable | Not applicable | 6.84E−10 | Not applicable |
| PRO811 (scDb) | 6.33E−09 | Not determined | Not determined | Not applicable |
| PRO624 (scDb) | 2.93E−09 | 2.39E−09 | Not applicable | 1.16E−10 |
| PRO746 (MATCH) | 3.52E−09 | 3.19E−09 | 1.41E−10 | 2.49E−11 |
| PRO733 | 2.65E−08 | 4.77E−08 | 4.95E−10 | 3.66E−11 |
| PRO734 | 1.19E−08 | 1.02E−08 | 4.82E−10 | 3.60E−11 |
| PRO736 | 1.11E−08 | 8.37E−09 | 6.35E−10 | 4.82E−11 |
| PRO737 | 2.40E−08 | 5.67E−08 | 4.93E−10 | 3.34E−11 |
| PRO738 | 1.01E−08 | 8.48E−09 | 3.03E−10 | 3.37E−11 |
| PRO739 | 1.23E−08 | 1.52E−08 | 2.28E−10 | 2.88E−11 |
| PRO741 | 7.58E−09 | 1.08E−09 | 3.38E−10 | 3.78E−11 |
| PRO747 | 8.30E−09 | 6.64E−09 | 3.25E−10 | 3.83E−11 |

| Protein ID | Affinity to human CD3 [M] | HER2 [M] | Affinity to HSA [M] | Affinity to IL23R [M] |
| --- | --- | --- | --- | --- |
| PRO320 HER2 | | 1.83E−10 | | |
| PRO821 PRO824 | 1.64E−09 | 6.13E−11 | | 3.03E−10 |

Affinities of hetero-dimeric MATCH constructs to each of the targets was generally very similar to the affinities of the individual binding domains measured in the scFv or scDb format. Notably the apparent affinity of the MATCH construct to IL23R appears increased in comparison to the scDb reference molecule, which can be explained by the avidity effect resulting from the incorporation of two IL23R binding domains in each MATCH molecule.

These data demonstrate maintained binding activity for each variable domain in the MATCH constructs and confirms correct assembly of the cognate variable domain pairs irrespective of the choice of core linkers, location of the interchain disulfide, the anti-CD3, anti-HSA domains used or attached scFv modules.

Certain differences in the affinities to the targets of the core-domain were observed for the various constructs. For the constructs containing a disulfide bond in the VL/VH interface of the CD3 domain, the charged core linker combination (comprising SEQ16 and SEQ17) used in PRO746 showed best affinity.

T-Cell Activation by NFAT Reporter Gene Assay
NFAT Assay

A CHO-K1 cell line stably expressing the human IL23R IL12Rbeta 1 heterodimer under control of a CMV promoter was generated by lentiviral transduction of the parental CHO-K1 cell line. These cells were used as target cells in the NFAt reporter gene assay while the parental CHO-K1 cell line was uses as control. 25,000 viable target cells diluted in 50 µl assay medium (RPMI 1640, 10% FCS) containing 25 g/L human serum albumin (HSA) were plated in white flat bottom 96-well plates. Then, 25 µl of 4 times concentrated test proteins diluted in assay medium containing HSA (25 g/L) were added to appropriate wells. Finally, 25 µl of assay medium with HSA containing 50,000 Jurkat cells was added to each well and plates were incubated at RT for 10 min with gentle agitation. One plate was made for each time point such as 5 h, 22 h or 30 h corresponding to the incubation times at 37° C., 5% CO2. In order to detect luciferase activity, one step luciferase assay kit (Amsbio) was used according to manufacturer's instructions. Briefly, at the end of the incubation times, luciferase reagent substrate was mixed with the luciferase reagent buffer and 50 µl were added to each well and plates were incubated for 15 min in the dark at RT. Plates were read with the TopCount™ analyzer (PerkinElmer©).25,000 viable target cells diluted in 50 µl assay medium (RPMI 1640, 10% FCS) were plated in white flat bottom 96-well plates. Then, 25 µl of 4 times concentrated test proteins diluted in assay medium were added to appropriate wells. Finally, 25 µl of assay medium containing 50,000 Jurkat cells was added to each well and plates were incubated at RT for 10 min with gentle agitation. One plate was made for each time point such as 5 h, 22 h or 30 h corresponding to the incubation times at 37° C., 5% CO2 either containing physiological concentrations of human serum albumin or not. In order to detect luciferase activity, one step luciferase assay kit (Amsbio) was used according to manufacturer's instructions. Briefly, at the end of the incubation times, luciferase reagent substrate was mixed with the luciferase reagent buffer and 50 µl were added to each well and plates were incubated for 15 min in the dark at RT. Plates were read with the TopCount™ analyzer (PerkinElmer®).

IL-2 Quantification by ELISA

100 µl supernatants were collected at different time points during the NFAT reporter gene assay from the wells containing 250 nM of the test molecules. IL-2 quantification was done using the IL-2 ELISA MAX™ Standard kit (Biolegend®) according to manufacturer's instructions. Briefly, 100 µl of capture antibody diluted in dilution buffer (PBS, 1% BSA, 0.2% polysorbate 20 (Tween© 20) was coated on 96-well plates Maxisorb (Nunc) over night at 4° C. Next day, plates were washed 3 times with wash buffer (PBS, 0.005% polysorbate 20 (Tween® 20). Wells were blocked with 300 µl dilution buffer for 1 h at RT, then washed 3 times with wash buffer. Next, 100 µl supernatant of the tested samples as well as 100 µl of each concentrations of the standard curve were added to the appropriate wells and plates were incubated for 2 h at RT with shaking. Plates were washed 3 times with wash buffer prior to incubation with the detection antibody for 1 h at RT with shaking. Plates were washed again 3 times with wash buffer and 100 µl Avidin-HRP was added to each well and incubated at RT for 30 min with shaking. Tree final washes were performed before addition of 100 µl TMB substrate solution. Plates were incubated for 15 minutes in the dark and reaction was stopped by adding 100 µl of Stop solution to each well. Absorbance was read at 450 nm and 570 nm. Absorbance at 570 nm was subtracted from the absorbance at 450 nm.

Results

TABLE 4

Tabulated data of the T-cell activation assay at 5 h timepoint for the different MATCH constructs relative to an on-plate reference CD3/HSA scDb (PRO389)

| Protein ID | NFAT assay EC50 | NFAT assay relative EC50 (to PRO389) |
|---|---|---|
| PRO389 (scDb) | 204 ± 44 pM | 1 |
| PRO624 (scDb) | 191 pM | 0.72 |
| PRO746 | 190 pM | 0.72 |
| PRO733 | 152 pM | 0.94 |
| PRO734 | 46820 pM | 261.6 |
| PRO736 | na | na |
| PRO737 | na | na |
| PRO738 | 423 pM | 2.34 |
| PRO739 | 442 pM | 2.44 |
| PRO741 | 6509 | 35.96 |
| PRO747 | 1450 pM | 7.63 |

Functional analysis of the MATCH construct variants in the NFAT reporter gene assay after 5 h of incubation showed the potency to activate T-cells. For comparison across different plates the data was normalized to an on-plate reference.

For the further in-depth characterization, the highest affinity MATCH construct (for CD3) PRO746, which also showed the best potency to activate T-cells, was used. In addition, constructs PRO821 and PRO824 were used a) to evaluate the functional activity of the HSA/CD3 core domain in the context of a different targeting domain (in this case anti-Her2), and b) to evaluate the alternative positioning of the disulfide bond in the HSA-binding domain instead of the anti-CD3 domain.

Figure 2:
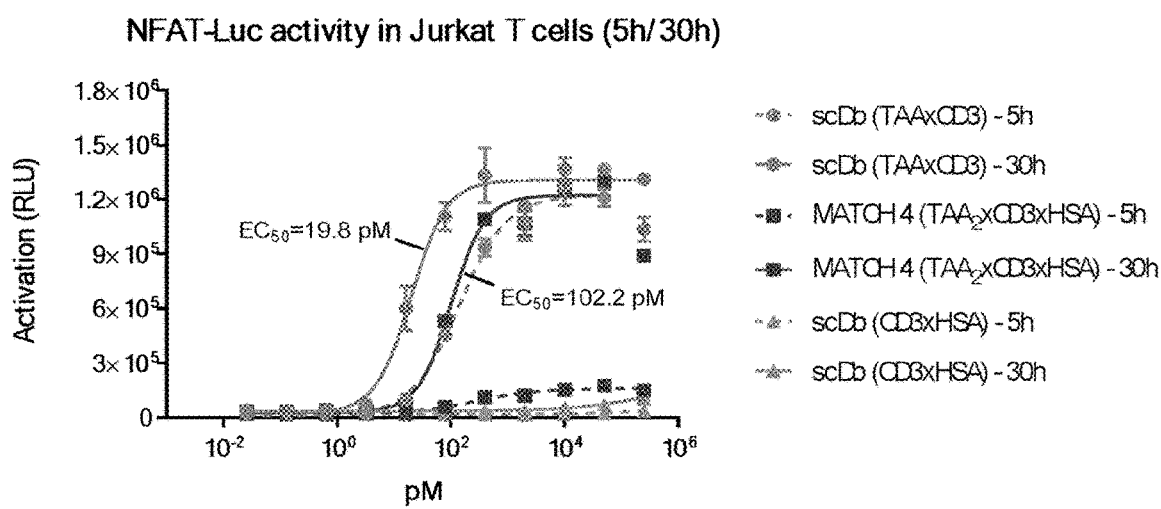
Figure 3:
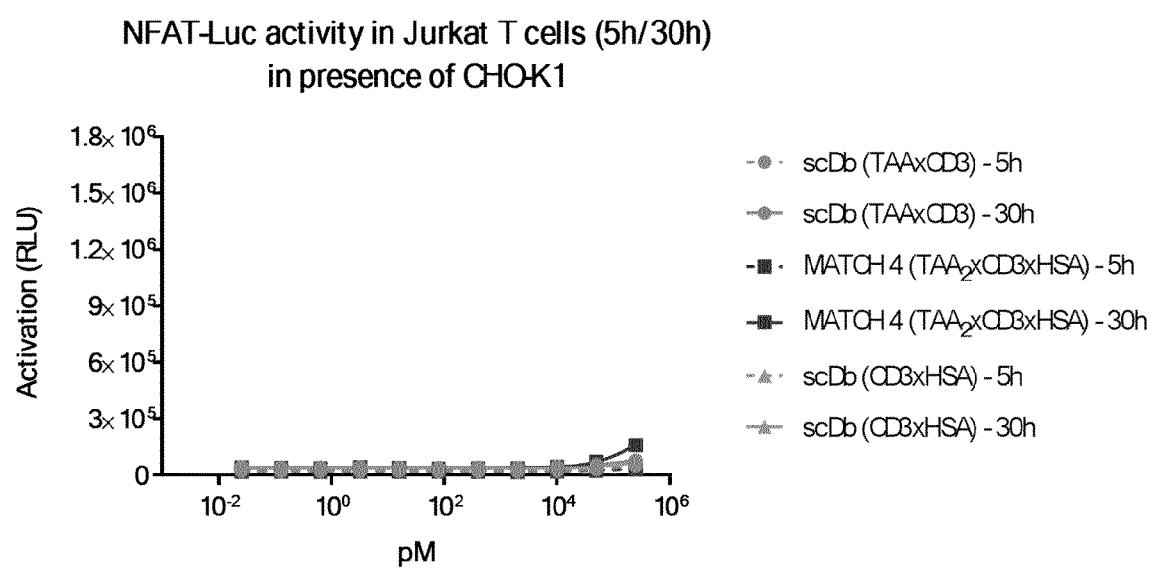
FIG. 3 shows the dose response of the T-cell activation in the presence of control cells at different concentrations of MATCH and reference scDb molecules.
Figure 4:
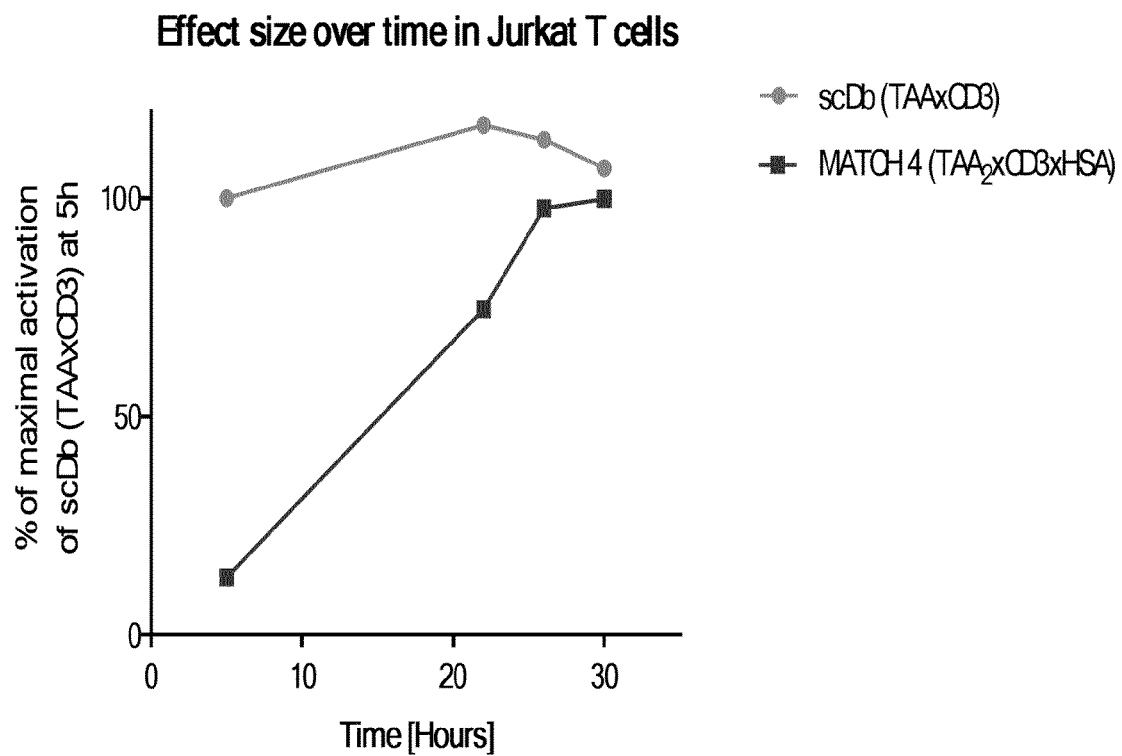
FIG. 4 shows a plot of the maximal activation of the T-cells induced by the MATCH and the scDb reference molecule normalized to the signal amplitude of the scDb at 5 h.

The potency of the molecules to activate T-cells in the presence of antigen-bearing target cells and physiological concentrations of human serum albumin (HSA) was determined over multiple timepoints and molecule concentrations (see FIG. 2). The heterodimeric MATCH (PRO746) was compared to a bispecific scDb with specificities for CD3ε and IL23R (PRO624) and a bispecific scDb combining the specificities present in the MATCH heterodimerization core (CD3ε and HSA) as a negative control (PRO811). The data shows that while negative control shows nearly no activation of T-cells, the scDb PRO624 shows strong activation of T-cells in presence of target cells expressing IL23R, at both the early and late timepoint. The signal amplitude reaches saturation at both timepoints and the EC50 improves approximately seven-fold from 5 to 30 h incubation (from 141.8 µM to 19.8 µM). Interestingly approximately five-fold from 5 to 30 h incubation. Interestingly the MATCH molecule, PRO746, shows a pronounced time-dependence in the T-cell activation. While the 5 h response only shows a low signal amplitude the response with the MATCH-4 reaches a very similar signal amplitude as with the scDb of the scDb after 30 h. The EC50 remains roughly five-fold higher than for the scDb over all time points (266.3 µM after 5 h and 102.2 µM after 30 h) (see points (see FIG. 4). Thus the two formats differ mainly in the kinetics of T cell activation (see also FIG. 3) rather than in their maximal activation potential.

The plot of the T-cell activation for the different molecules in the presence of cells devoid of the target protein (FIG. 3) shows nearly no activation of T-cells, even at concentrations far above the EC50 for T cell activation in presence of target cells. This together with the lack of T cell activation with PRO811, confirms the requirement of target cell binding for T cell activation for the molecules containing the HSA/CD3-core domain. The lack of unspecific activation of T-cells is prerequisite to avoid unwanted side effects by T-cell recruiting therapies.

The plot of the plateau values of the dose response signals at different timepoints (FIG. 4) shows that the reference scDb (PRO624) induces a nearly maximal signal amplitude already at 5 h incubation. On the other hand, the signal amplitude induced by the MATCH molecule starts at below 20% of the value of the scDb, however, steadily increases over time to finally reach the same level of T cell activation after 30 h of incubation.

Figure 5:
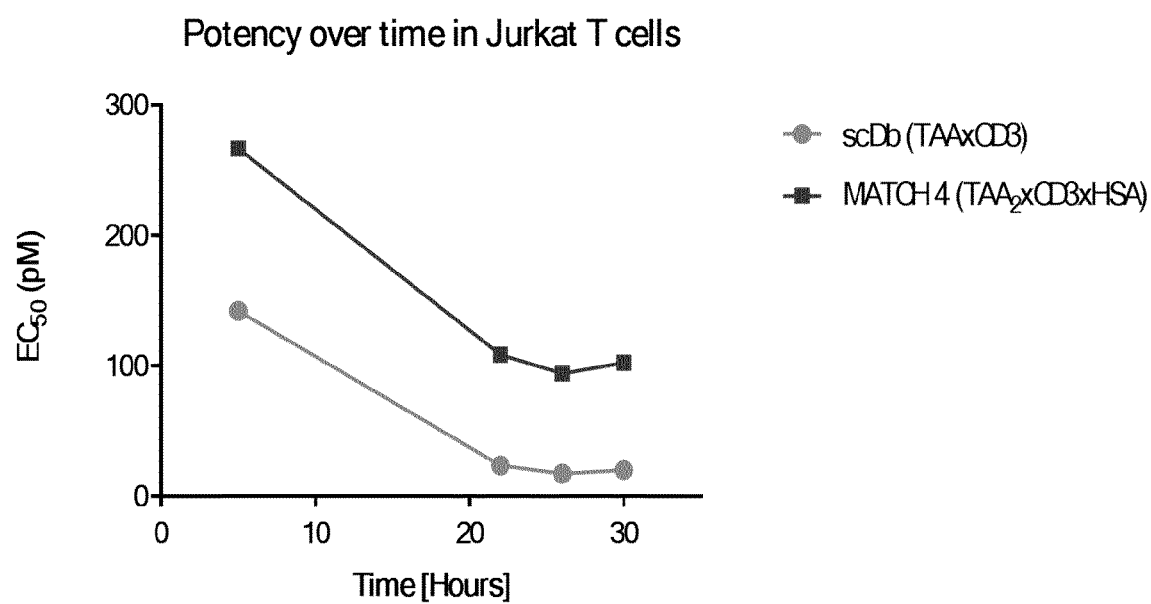
FIG. 5 shows a plot of the potency of the test molecules over the time of the study.

The plot of the EC50 values of the dose response curves for the scDb and MATCH molecule (FIG. 5) show an improvement of the EC50 over the course of the time, interestingly however, the improvement of the EC50 follows a very similar pattern for both molecules, and the curves run in parallel to each other. Thus, the kinetics for potency (EC50) are similar for both, the small scDb and the larger MATCH containing a HSA-binding domain. However, the kinetics for maximal T cell activation strongly differ in that the MATCH shows a slower activation.

Figure 6:
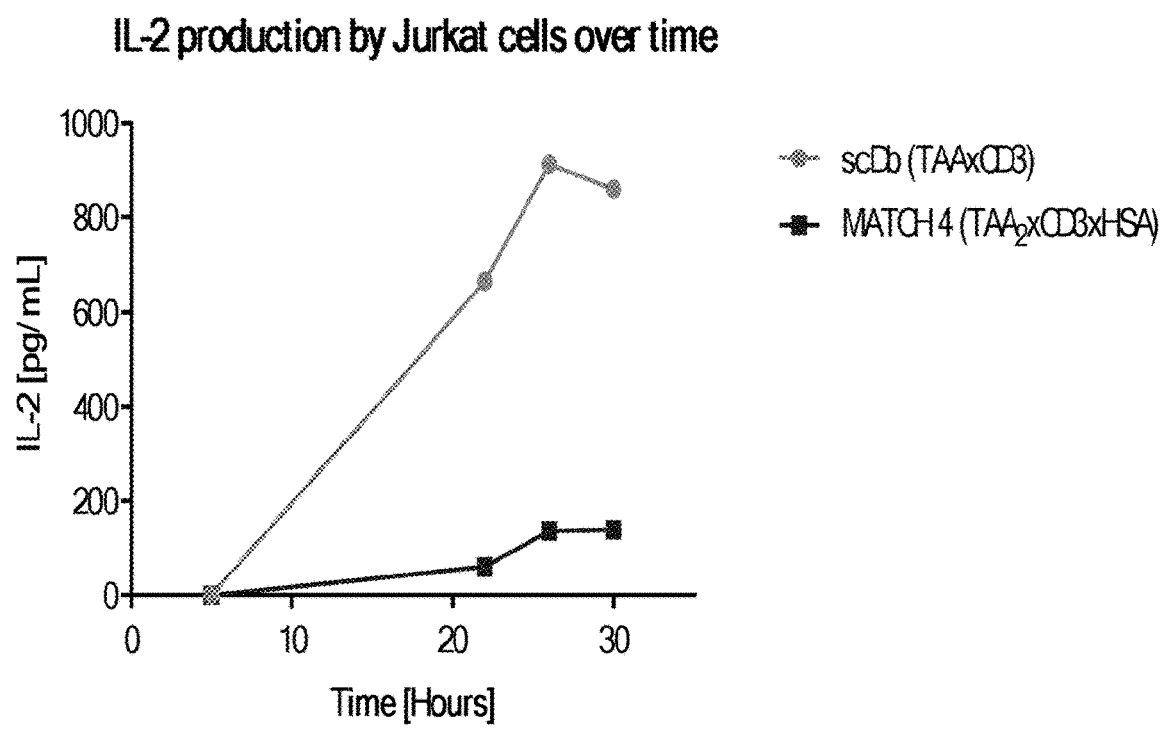
FIG. 6 shows the determination of the IL-2 concentration of the NFAT activation assay at different timepoints by ELISA.

The release of T-cell activation marker IL-2 was quantified for the samples of the NFAT reporter gene assay of the molecules PRO624 (scDb) and PRO746 (MATCH) (see FIG. 6). For the scDb reference molecule a strong increase of IL-2 concentration is observed during the 30 h incubation. Interestingly the amount of IL-2 present in the wells with the MATCH molecules was considerably lower for all timepoints even after 30 h when the corresponding T-cell activation signal was nearly identical.

In summary, our findings indicate that the MATCH format comprising the HSA/CD3 core-domain has the same capacity to activate T cells, with a slower activation kinetic, though. This is interesting in the light of the fact, that side effects associated with cytokine release with other T cell engaging bispecifics (e.g. blinatumomab/blincyto) are strongest during the early times of dosing. In fact, only low doses of blinatumomab/blincyto are tolerated at the beginning of the therapy, while considerably higher doses are tolerated afterwards. A probable explanation for this is the strong cytokine burst that occurs immediately after dosing that may lead to the so-called cytokine release syndrome (CRS). Therefore, the MATCH presented here, due to its slow T cell activation kinetics and consequential reduced cytokine release is likely to lead to reduced toxicities, whereas it has the capacity to reach the same level of T cell activation over time. In addition, the reduction of cytokine release even at similar levels of T-cell activation is an even more surprising feature of PRO746, which suggests to reduce occurrence of the frequently observed cytokine release syndrome associated with T-cell recruiting therapies further.

Cytotox Assay (T-Cell Driven Target Cell Depletion)
Blood Cells Fractionation

Peripheral blood mononuclear cells (PBMC) were isolated from fresh blood of healthy volunteers using the lymphocyte separation medium Lymphoprep® (Stemcell Technologies®) according to manufacturer's instructions. Briefly, blood was diluted 1:1 with isolation buffer in 50 ml centrifuge tubes (PBS, 2% FCS, 2 mM EDTA) and applied to separation tubes (Leucosep™) containing recommended amount of Lymphoprep® medium. LeucoSep™ tubes were centrifuged 30 min at 800 g without brakes at RT. Then, the cell layer containing PBMCs was collected and washed twice with isolation buffer and red blood cells were lysed using red blood cells lysis buffer for 5 min at RT. Cells were then washed once with isolation buffer and once with assay medium (RPMI-1640, 10% FCS). After platelet removal, isolated PBMCs were resuspended in assay medium containing 25 g/ml HSA at a density $3\times10^6$ viable cells per ml.

Flow Cytometry-Based In Vitro Cytotoxicity Assay and CD8+ T Cells Activation

A CHO-K1 cell line stably expressing the human IL23R IL12Rbeta 1 heterodimer under control of a CMV promoter was generated by lentiviral transduction of the parental CHO-K1 cell line. These cells were used as target cells in the cytotoxicity assay while the parental CHO-K1 cell line was uses as control. Additionally, a CHO-K1 cell line stably expressing human HER2 was as well generated by lentiviral transduction of parental CHO-K1 cells with full-length HER2 cDNA. Expression levels of HER2 and the IL23R were determined by flow-cytometry. HER2 levels at the cell surface are much higher compared to IL23R levels. 5,000 viable target cells previously labelled with PKH67 and diluted in 75 µl of assay medium (RPMI-1640, 10% FCS) containing 25 g/L human serum albumin (HSA) were added to 96-well plates. Next, 25 µl of 6 times concentrated tested proteins diluted in assay medium with HSA were added to appropriate wells. Then, in order to have an E:T ratio of 30:1, 150,000 viable effector cells (PBMCs) diluted in 50 µl assay medium containing HSA were added to each well and plates were mixed on a nutating mixer at RT prior to their incubation at 37° C., 5% CO2. After 16 h, cells were trypsinized, resuspended in staining buffer (PBS, 2% BCS, 2 mM EDTA) and transferred into non-binding plates.

Cells were stained for different markers as CD69, CD8, CD4, CD11c and Annexin-V. For analysis, the focus is on apoptotic and dead target cells and activated CD8+ T cells. Thereby, target cells are identified by green fluorescence (PKH67) and their viability is analyzed by Annexin-V APC. Effector cells (CD8+ cells) were identified by detecting CD8 on their surface (anti-CD8 PerCP-Cy5.5). Activation of CD8+ T cells is finally detected by quantification of CD69 expression (anti-CD69 PE). CD4 is used to better discriminate CD8+ and CD4+ T cells. CD11c is used to mark monocytes and dendritic cells and exclude them. For each marker except Annexin-V antibodies are incubated 30 minutes at RT under gentle agitation. Cells are washed once with staining buffer, once with Annexin binding buffer and Annexin-V staining is carried on for 30 minutes at RT under agitation. Cells are washed once with Annexin-V binding buffer and flow cytometry analysis was done on a Novocyte® Flow Cytometer.

The percentage of specific target cells lysis is calculated according to the following equation:

$$\text{Specific lysis of target cells [in \%]} = \left[1 - \frac{\text{Viability target cells of sample}}{\text{average viability of control samples}}\right] \times 100$$

The percentage of activated CD8+ T cells correspond to the proportion of CD69+CD8+ T cells.

IL-2 Quantification by Flow Cytometry

IL-2 quantification in supernatant was performed using the cytometric bead array human Th1/Th2 cytokine kit II (BD® Biosciences) according to manufacturer's protocol. Briefly, 50 µl of the mixed Capture Beads were added to each supernatant analyzed as well as to the IL-2 standard dilutions. After 3 h hours incubation at RT in the dark, beads were washed 3 times with wash buffer and analyzed by flow cytometry on a Novocyte® instrument.

Results

Figure 7:
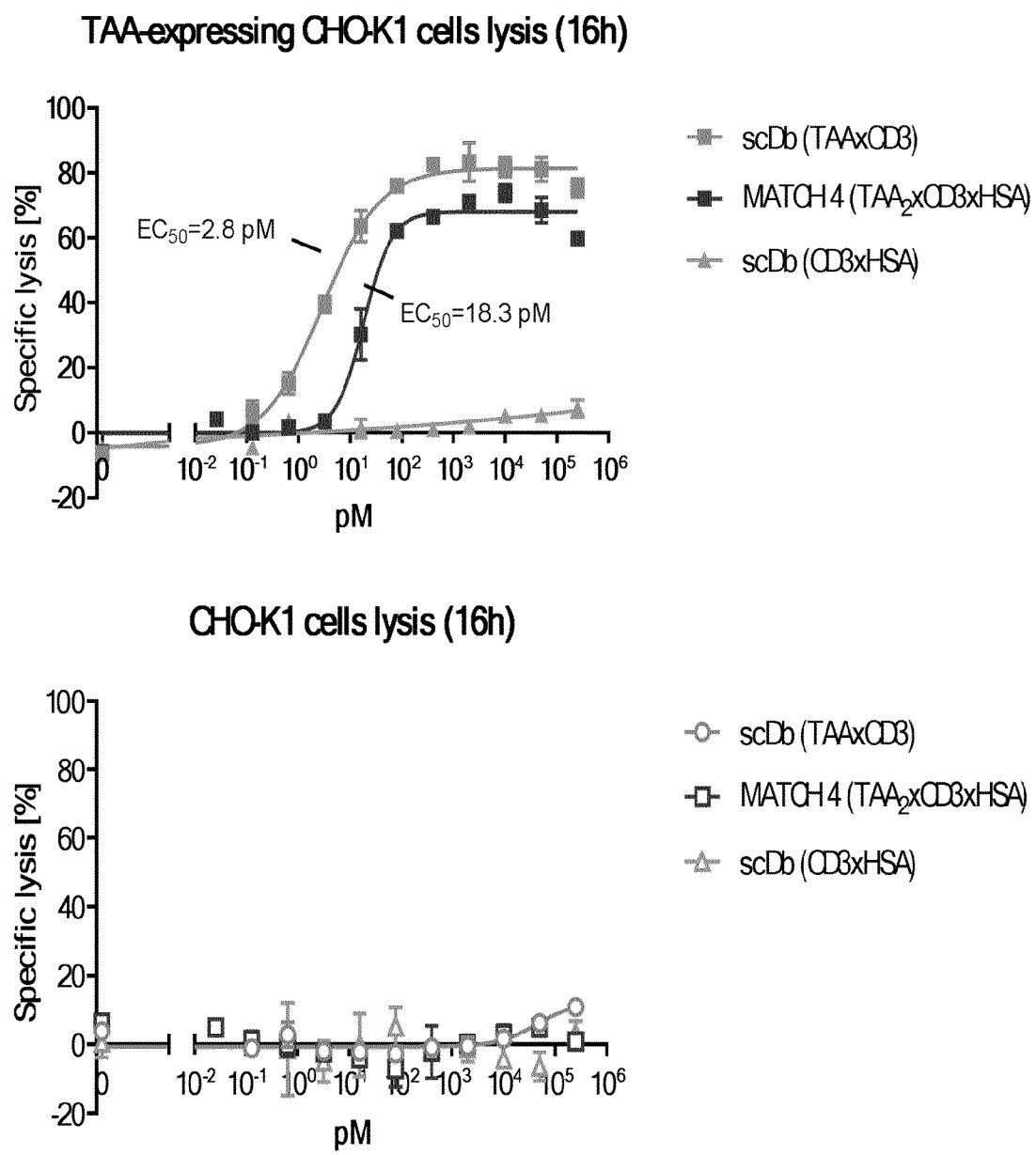
FIG. 7 shows the dose-response plots of the cell lysis for the MATCH and the two reference scDb. The left panel shows the specific lysis of IL23R expressing target cells, while the right panel shows no specific lysis of IL23R negative cells.

The cell lysis data shows the specific potency and specificity of both molecules PRO746 (MATCH-4 anti-TAA2xCD3xHSA) and PRO624 (scDb; anti-TAAxCD3) to induce depletion of target-bearing cells, while the negative control PRO811 (scDb; anti-CD3xHSA) fails to induce target cell lysis (see FIG. 7). In agreement with the NFAT assay shown above, the EC50 of the response with the MATCH molecule is slightly shifted to higher concentration compared to the scDb, while a similar fraction of target cells is lysed after 16 hours of incubation.

Figure 8:
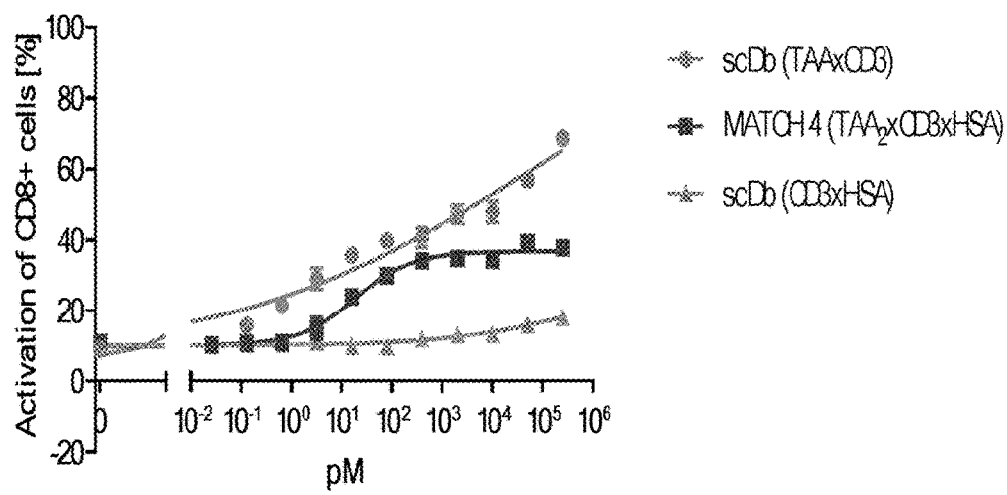
FIG. 8 shows the dose-response plot of the fraction of activated T-cells. The left panel shows the fraction of activated T-cells in the presence of IL23R expressing target cells, while the right panel shows the activated T-cells in the presence of IL23R negative cells.
Figure 8:
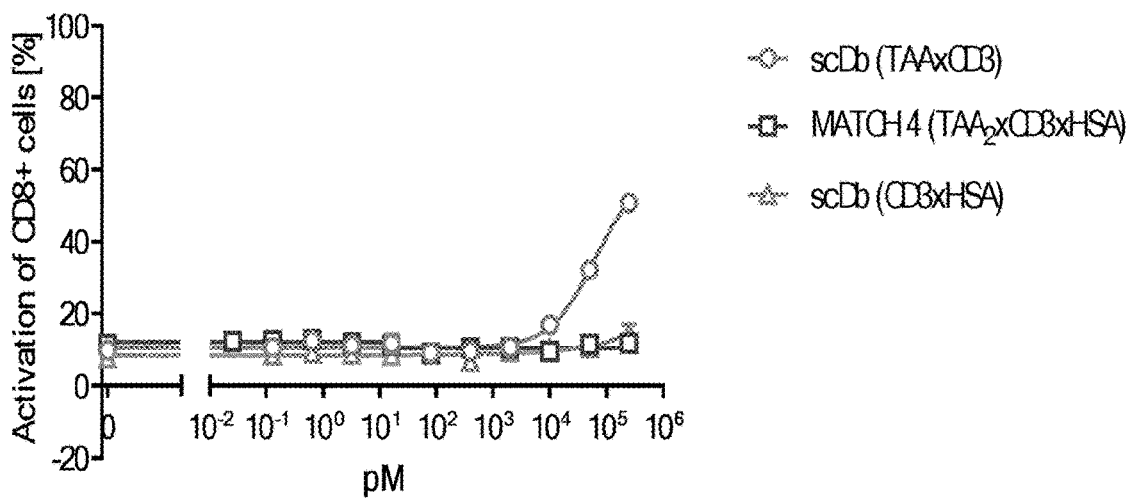

The quantification of the T-cell activation in the dose-response of the three molecules is consistent with the observations of cell lysis (see FIG. 8). With this read-out a signal of unspecific T-cell activation is seen with the CD3/IL23R scDb (PRO624) in the absence of target expressing cells. The MATCH on the other hand does not show any signs of unspecific T-cell activation up to the highest concentrations tested.

Figure 9:
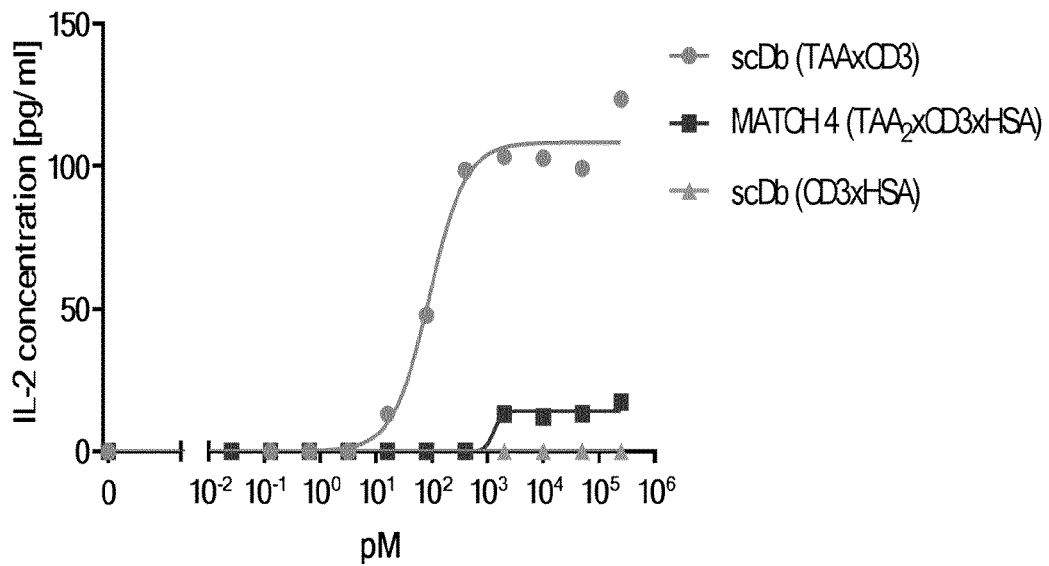
FIG. 9 shows the dose-response of the IL-2 concentration in the respective wells of the cytotox assay induced by the T-cell activation. The left panel shows concentration of IL-2 induced in the presence of IL23R expressing target cells, while the right panel shows IL-2 concentration of IL-2 induced in the presence of IL23R negative cells.
Figure 9:
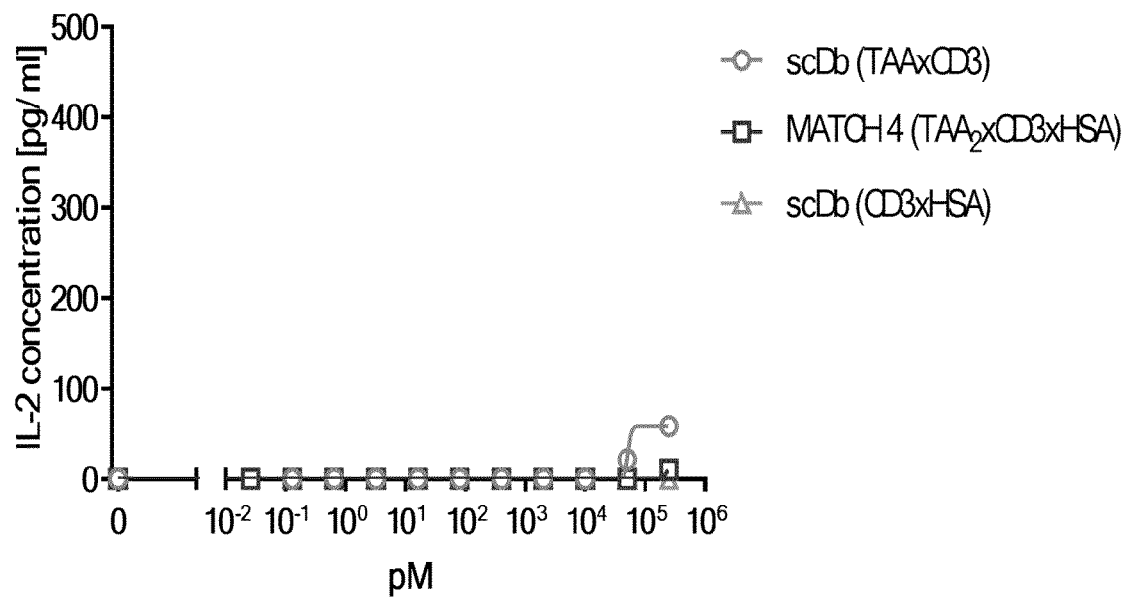

The concentrations of IL-2 in the wells were measured (FIG. 9). The maximum concentration of IL-2 is strikingly different for both molecules with the MATCH resulting in a considerably lower plateau of IL-2. In the quantifications of the wells with the target-negative cell line only the CD3/IL23R scDb results in an increase of IL-2 concentration at the highest tested concentrations of scDb. In line with data shown in the NFAT reporter gene assay above, the data in FIG. 8 confirm the reduced release of cytokines with the MATCH (PRO746) comprising an CD3/HSA-core domain in presence of HSA, when compared to the scDb (PRO624). Importantly, both molecules have similar capacities to trigger target cell lysis, while their capacity for maximal target cell lysis are similar.

Figure 10:
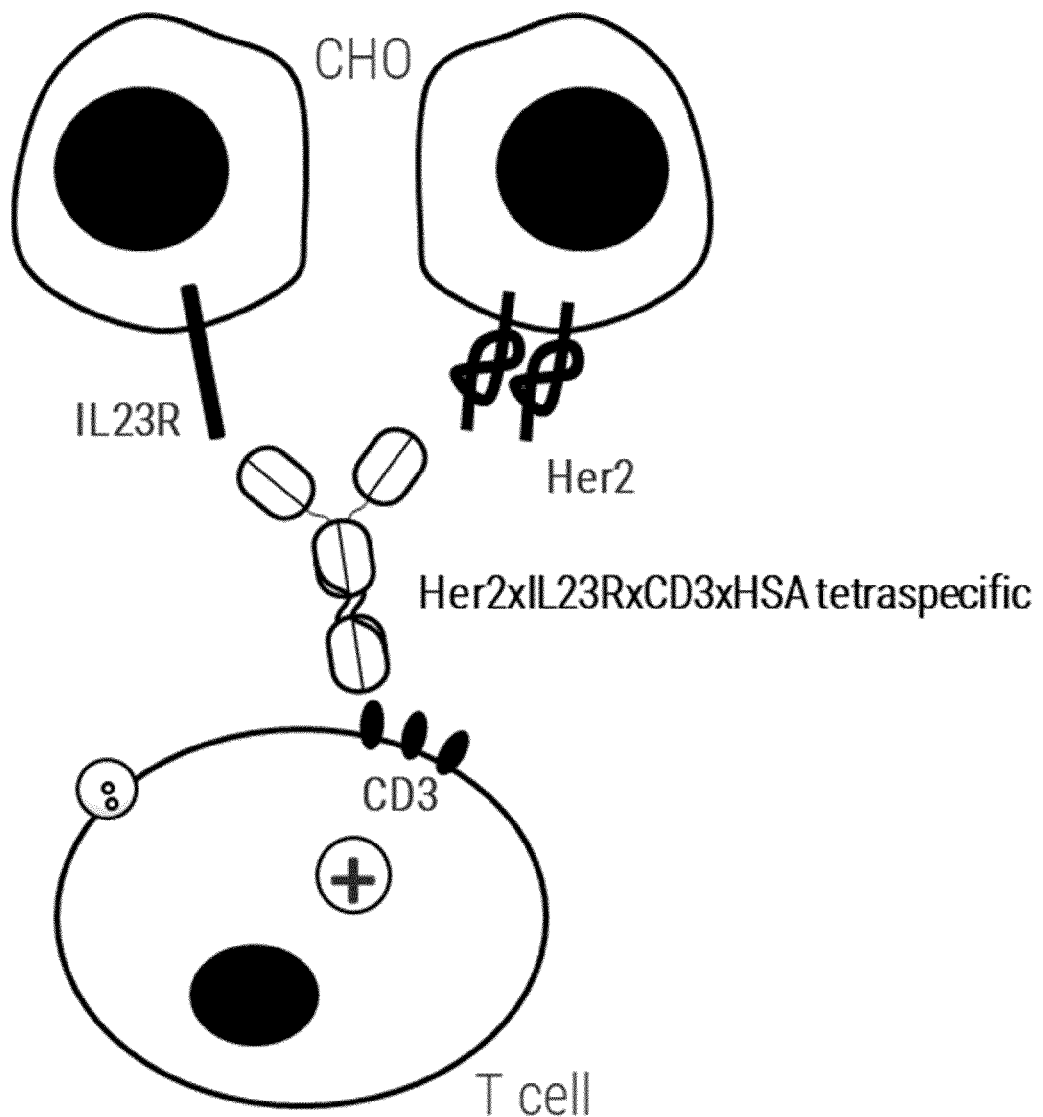
FIG. 10 shows a schematic outline of the dual targeting using a MATCH with a anti-CD3/anti-HSA heterodimeric core assembly.

The tetraspecific assemblies were generated to show the potential of the MATCH assemblies with a CD3/HSA heterodimerization core to be used to combine two antigen specificities of tumor associated antigens of different expression profiles (see FIG. 10). The data shows that both specificities of the "peripheral" scFv attached to the CD3/HSA-core domain can be exploited to efficiently drive T-cell mediated depletion of two different target cell populations by one single molecule (see FIG. 11). It also shows the effect of different target expression on the observed dose response curves, namely that lower target expression shifts the response to higher concentrations, which can be reversed by providing multivalent binding of the low expressing targets, as shown in FIG. 6. For high expressing targets, on the other hand, already monovalent antigen binding results in highly potent target cell depletion. Such dual targeting can further be exploited to increase the specificity of the mechanism of action by preferential targeting of the molecule to cells that co-express two cell surface targets rather than cells exclusively expressing one of the two target. In order to achieve this, a range of binders with varying affinities to either of the two targets can be tested in all possible combinations using the MATCH format comprising the CD3/HSA-core domain presented herein, to select the one combination with optimal specificity in cell-lysis (see Egan et al. mAbs. 2016).

The invention claimed is:

1. A hetero-dimeric protein comprising a first and a second single-chain protein,
   wherein said first single-chain protein comprises a first amino acid sequence consisting of, from the N- to the C-terminus:
   (ia) a first VL domain,
   (iia) a first polypeptide linker, and
   (iiia) a second VL domain, and
   wherein said second single-chain protein comprises a second amino acid sequence consisting of, from the N- to the C-terminus:
   (ib) a first VH domain,
   (iib) a second polypeptide linker, and
   (iiib) a second VH domain, and
   wherein said first VL domain forms a first cognate pair of variable domains with specificity to a first target antigen with either said first or said second VH domain, and said second VL domain forms a second cognate pair of variable domains with specificity to a second target antigen with the other of said VH domains, wherein one of said target antigens is human serum albumin and the other said target antigen is human CD3,
   and wherein at least one of said first and said second single-chain proteins further comprises
   (iv) at least one additional antibody-based binding domain as third functional domain that is fused via a third polypeptide linker to said first or said second amino acid sequence at the N-terminus or the C-terminus;

wherein said cognate pair of variable domains with specificity for human serum albumin comprises the three VL CDRs present in one of the VL protein sequences selected from the group consisting of SEQ ID NOs: 10, 12 and 14 in a human antibody VL framework, wherein the VL framework has a 95% sequence identity to the VL framework regions FR1, FR2, FR3 and FR4 of one of the VL protein sequences selected from the group consisting of SEQ ID NOs: 10, 12 and 14, and the three VH CDRs present in one of the VH protein sequences selected from the group consisting of SEQ ID NOs: 11, 13, and 15 in a human antibody VH framework, wherein the VH framework has a 95% sequence identity to the VH framework regions FR1, FR2, FR3 and FR4 of one of the VH protein sequences selected from the group consisting of SEQ ID NOs: 11, 13 and 15; and wherein said cognate pair of variable domains with specificity for human CD3 comprises the three VL CDRs present in one of the VL protein sequences selected from the group consisting of SEQ ID NOs: 2, 4, 6 and 8 in a human antibody VL framework, wherein the VL framework has a 95% sequence identity to the VL framework regions FR1, FR2, FR3 and FR4 of one of the VL protein sequences selected from the group consisting of SEQ ID NOs: 2, 4, 6 and 8, and the three VH CDRs present in one of the VH protein sequences selected from the group consisting of SEQ ID NOs: 3, 5, 7 and 9 in a human antibody VH framework, wherein the VH framework has a 95% sequence identity to the VH framework regions FR1, FR2, FR3 and FR4 of one of the VH protein sequences selected from the group consisting of SEQ ID NOs: 3, 5, 7 and 9.

2. The hetero-dimeric protein of claim 1, wherein said hetero-dimeric protein does not comprise a cognate pair of a first and a second immunoglobulin constant domain, wherein said first immunoglobulin constant domain is comprised in said first single-chain protein and wherein said second immunoglobulin constant domain is comprised in said second single-chain protein.

3. The hetero-dimeric protein of claim 1, further comprising
(v) a fourth functional antibody-based binding domain that is fused via a fourth polypeptide linker to said first or said second amino acid sequence;
(vi) a fourth and a fifth functional antibody-based binding domain that are fused via a fourth and a fifth polypeptide linker, respectively, to said first and said second amino acid sequence; or
(vi) a fourth, a fifth and a sixth functional antibody-based binding domain that are fused via a fourth, a fifth and a sixth polypeptide linker, respectively, to said first and said second amino acid sequence.

4. The hetero-dimeric protein of claim 1, wherein said first polypeptide linker consists of from 5 to 20 amino acid residues.

5. The hetero-dimeric protein of claim 1, wherein said first single-chain protein and said second single-chain protein hetero-dimerize in a parallel orientation, where said first and said second single-chain proteins associate both in N- to C-terminal or C- to N-terminal order.

6. The hetero-dimeric protein of claim 1, wherein said first single-chain protein and said second single-chain protein hetero-dimerize in an anti-parallel orientation, where one of said first and second single-chain proteins associates in N- to C-terminal order with the other single-chain protein in C- to N-terminal order.

7. The hetero-dimeric protein of claim 6, wherein said first and said second polypeptide linker each consists of from 10 to 20 amino acid residues comprising between 40 and 60% charged residues, wherein the two linkers are able to interact by forming interchain pairs of positively and negatively charged residues.

8. The hetero-dimeric protein of claim 1, wherein (a) said first VL domain (ia) and said first VH domain (ib) form a first cognate pair of variable domains with specificity to human serum albumin, and said second VL domain (iia) and said second VH domain (iib) form a second cognate pair of variable domains with specificity to human CD3; or (b) said first VL domain (ia) and said second VH domain (iib) form a first cognate pair of variable domains with specificity to human CD3, and said second VL domain (iia) and said first VH domain (ib) form a second cognate pair of variable domains with specificity to human serum albumin.

9. The hetero-dimeric protein of claim 1, wherein at least one of said antibody variable domains comprises CDR regions derived from a parental rabbit antibody.

10. The hetero-dimeric protein of claim 1, wherein said first single-chain protein and said second single-chain protein are cross-linked by at least one disulfide bond.

11. The hetero-dimeric protein of claim 10, wherein said disulfide bond is formed between a first cysteine residue flanking said first or said second VL domain and a second cysteine residue flanking said first or said second VH domain.

12. The hetero-dimeric protein of claim 10, wherein said disulfide bond is formed between a first cysteine residue comprised in a framework region of said first or said second VL domain and a second cysteine residue comprised in a framework region of said first or said second VH domain.

13. The hetero-dimeric protein of claim 12, wherein said first cysteine residue is located at position 141 according to the AHo numbering system of said first or said second VL domain and said second cysteine residue is located at position 51 according to the AHo numbering system of said first or said second VH domain.

14. The hetero-dimeric protein of claim 1, wherein said cognate pair of variable domains with specificity for human serum albumin comprises a VL domain comprising at least positions 5 to 140 according to the AHo numbering system of a protein sequence selected from the group consisting of SEQ ID NOs: 10, 12, and 14, and a VH domain comprising at least positions 5 to 140 according to the AHo numbering system of a protein sequence selected from the group consisting of SEQ ID NOs: 11, 13, and 15.

15. The hetero-dimeric protein of claim 1, wherein said cognate pair of variable domains with specificity for human CD3 comprises a VL domain comprising at least positions 5 to 140 according to the AHo numbering system of a protein sequence selected from the group consisting of SEQ ID NOs: 2, 4, 6 and 8, and a VH domain comprising at least positions 5 to 140 according to the AHo numbering system of a protein sequence selected from the group consisting of SEQ ID NOs: 3, 5, 7 and 9.

16. A method for producing the hetero-dimeric protein of claim 1, or the first and the second single-chain proteins of said hetero-dimeric protein, comprising providing the nucleic acid sequence or the two nucleic acid sequences encoding the first and the second single-chain proteins of the hetero-dimeric protein claim of 1 expressing said nucleic acid sequence or nucleic acid sequences, and collecting said hetero-dimeric protein from the expression system.

17. A pharmaceutical composition comprising the hetero-dimeric protein of claim 1 and a pharmaceutically acceptable carrier.

18. A method for the treatment of a human disease selected from cancer, an inflammatory and an autoimmune disease, comprising the step of administering the hetero-dimeric protein of claim 1.

19. The hetero-dimeric protein of claim 4, wherein said first polypeptide linker consists of from 6 to 15 amino acid residues.

20. The hetero-dimeric protein of claim 7, wherein said first and said second polypeptide linker each consists of from 12 to 16 amino acid residues comprising 50% charged residues.

21. The hetero-dimeric protein of claim 7, wherein the charged residues on one of said first and second linkers are exclusively positively charged residues, and the charged residues on the other of said first and second linkers are exclusively negatively charged residues.

22. The hetero-dimeric protein of claim 7, wherein said first and second linkers are selected from SEQ ID NOs. 16 and 17.

23. The hetero-dimeric protein of claim 1, wherein said antibody-based binding domains are independently selected from scFv fragments and Fab fragments.

24. The hetero-dimeric protein of claim 14, wherein said cognate pair of variable domains with specificity for human serum albumin comprises (i) a VL domain comprising at least positions 3 to 145 according to the AHo numbering system of a protein sequence selected from the group consisting of SEQ ID NOs: 10, 12, and 14, (ii) a VH domain comprising at least positions 3 to 145 according to the AHo numbering system of a protein sequence selected from the group consisting of SEQ ID NOs: 11, 13, and 15, and/or (iii) a VL domain selected from the group consisting of SEQ ID NOs: 10, 12, and 14, and a VH domain selected from the group consisting of SEQ ID NOs: 11, 13, and 15.

25. The hetero-dimeric protein of claim 15, wherein said cognate pair of variable domains with specificity for human CD3 comprises (i) a VL domain comprising at least positions 3 to 145 according to the AHo numbering system of a protein sequence selected from the group consisting of SEQ ID NOs: 2, 4, 6 and 8, (ii) a VH domain comprising at least positions 3 to 145 according to the AHo numbering system of a protein sequence selected from the group consisting of SEQ ID NOs: 3, 5, 7 and 9, and/or (iii) a VL domain selected from the group consisting of SEQ ID NOs: 2, 4, 6 and 8, and a VH domain selected from the group consisting of SEQ ID NOs: 3, 5, 7 and 9.

* * * * *